(12) United States Patent
Tawada et al.

(10) Patent No.: US 7,323,577 B2
(45) Date of Patent: Jan. 29, 2008

(54) PROCESS FOR PRODUCING BENZOFURAN DERIVATIVE

(75) Inventors: Hiroyuki Tawada, Takatsuki (JP); Makoto Yamashita, Amagasaki (JP); Yujiro Ono, Suita (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 155 days.

(21) Appl. No.: 11/359,023

(22) Filed: Feb. 22, 2006

(65) Prior Publication Data

US 2006/0142598 A1 Jun. 29, 2006

Related U.S. Application Data

(62) Division of application No. 10/483,089, filed as application No. PCT/JP02/07045 on Jul. 11, 2002, now Pat. No. 7,034,166.

(30) Foreign Application Priority Data

Jul. 13, 2001 (JP) ............................. 2001-213665

(51) Int. Cl.
*C07D 493/00* (2006.01)
(52) U.S. Cl. .................... 549/469; 549/330; 549/331; 549/342; 549/343; 549/344; 549/345
(58) Field of Classification Search ............... 549/469, 549/330, 331, 343, 342, 344, 345
See application file for complete search history.

(56) References Cited

FOREIGN PATENT DOCUMENTS

| EP | 0 483 772 | 5/1992 |
|----|-----------|--------|
| WO | WO 00/02887 | 1/2000 |
| WO | WO 00/34262 | 6/2000 |
| WO | WO 01/12618 | 2/2001 |
| WO | WO 02/28850 | 4/2002 |

OTHER PUBLICATIONS

Kosugi, M., et al., "Palladium-Catalyzed Aromatic Amination of Aryl Bromides with N,N-Di-Ethylamino-Tributyltin", *Chemistry letters*, (1983), pp. 927-928.

*Primary Examiner*—Bernard Dentz
*Assistant Examiner*—David E Gallis
(74) *Attorney, Agent, or Firm*—Edwards Angell Palmer & Dodge LLP; David G. Conlin; Jacobson G. Weintraub

(57) ABSTRACT

A novel process for efficiently and easily producing a compound represented by the formula:

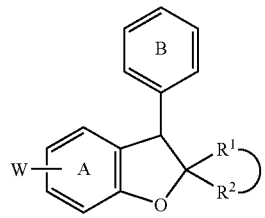

wherein ring A is a benzene ring that may be optionally further substituted in addition to the group represented by W, or a salt thereof; which comprises reacting a compound represented by the formula:

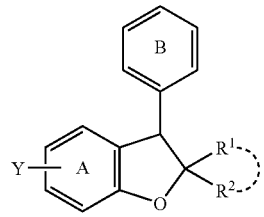

wherein $R^1$ and $R^2$ are the same or different and each is a hydrogen atom, an optionally substituted hydrocarbon group or an optionally substituted heterocyclic group, Y is a halogen atom, ring A is a benzene ring that may be optionally further substituted in addition to the group represented by Y and ring B is an optionally substituted benzene ring, or a salt thereof, with a compound represented by the formula:

WH wherein W is

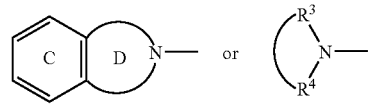

wherein ring C is an optionally substituted benzene ring, ring D is an optionally substituted 5- to 7-membered nitrogen-containing heterocyclic ring, $R^3$ is a hydrogen atom, an aliphatic hydrocarbon group containing an aromatic group or an acyl group, and $R^4$ is a hydrogen atom, an optionally substituted hydrocarbon group or an acyl group, or a salt thereof and thereafter, if necessary, deprotecting the resultant product, which is suitable for industrial production.

6 Claims, No Drawings

PROCESS FOR PRODUCING BENZOFURAN DERIVATIVE

This application is divisional of U.S. patent application Ser. No. 10/483,089, filed on Jan. 7, 2004 and now U.S. Pat. No. now U.S. Pat. No. 7,034,166 which was the National Phase filing of International Patent Application No. PCT/JP02/07045, filed Jul. 11, 2002.

TECHNICAL FIELD

The present invention relates to a process for producing a benzofuran derivative, in particular, a process for producing the compound having an amino or fused cyclic amino group which may be optionally substituted at the 5-position on 2,3-dihydrobenzofuran, which is industrially advantageous.

BACKGROUND ART

Derivatives having a 2,3-dihydrobenzofuran ring have been reported to have various pharmacological activities and an industrially advantageous process for synthesizing them has been widely sought. Methods for constructing a 2,3-dihydrobenzofuran ring include methods described, for example, in JP-A 5-194466, EP-A-483772, JP-A 5-140142 and WO98/08842. Many of compounds in which a substituted amino group is introduced into the 5-potision on a 2,3-dihydrobenzofuran ring have useful physiological activity and therefore they are important.

In order to introduce a substituted amino group into the 5-position on a 2,3-dihydrobenzofuran ring, as described in WO 00/34262, a method of constructing 2,3-dihydrobenzofuran using as starting material a phenol derivative in which a substituted amino group has been previously introduced into the desired position, and a method of synthesizing the desired compound by nitration or nitrosation of 2,3-dihydrobenzofuran in which the 5-position is not substituted followed by reduction reaction are known. In view of usefulness of 2,3-dihydrobenzofuran compounds, there is a need for provision of a process with high yield under milder reaction conditions, which is suitable for industrial production of these compounds.

OBJECTIVE OF THE INVENTION

In view of such circumstances, an objective of the present invention is to provide a novel process for producing a benzofuran derivative having a 2,3-dihydrobenzofuran ring, inter alia, a novel process for producing the compound having a substituted amino group or a benzene ring-fused cyclic amino group such as an isoindolyl group at the 5-potision on the 2,3-dihydrobenzofuran ring, which is efficient, simple and suitable for industrial production.

SUMMARY OF THE INVENTION

In order to attain the aforementioned objective, the present inventors intensively studied and, as a result, found an efficient and simple process for constructing a 2,3-dihydrobenzofuran ring and, at the same time, found that a 2,3-dihydrobenzofuran ring is position-selectively halogenated, in particular, at its 5-position and, further, this halogen atom is easily substituted with an amino derivative, which resulted in completion of the present invention.

That is, the present invention provides:

(1) a process for producing a compound represented by the formula:

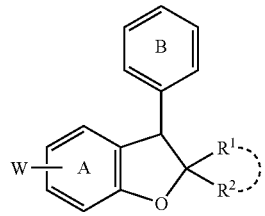

wherein ring A is a benzene ring that may be optionally further substituted in addition to the group represented by W and other symbols are as defined below, or a salt thereof; which comprises reacting a compound represented by the formula:

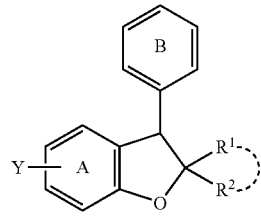

wherein $R^1$ and $R^2$ are the same or different and each is a hydrogen atom, an optionally substituted hydrocarbon group or an optionally substituted heterocyclic group, or $R^1$ and $R^2$ may be taken together with the adjacent carbon atom to form an optionally substituted 3- to 8-membered homocyclic or heterocyclic ring, Y is a halogen atom, ring A is a benzene ring that may be optionally further substituted in addition to the group represented by Y, and ring B is an optionally substituted benzene ring, or a salt thereof, with a compound represented by the formula:

WH wherein W is:

(i) a group represented by the formula:

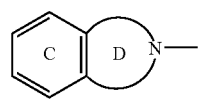

wherein ring C is an optionally substituted benzene ring and ring D is a 5- to 7-membered nitrogen-containing heterocyclic ring that may be optionally substituted with halogen or an optionally substituted hydrocarbon group, or (ii) a group represented by the formula:

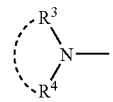

wherein $R^3$ is (1) a hydrogen atom, (2) an aliphatic hydrocarbon group that is substituted with an optionally substituted aromatic group and may be optionally further substituted, or (3) an acyl group containing an optionally substituted aromatic group; $R^4$ is a hydrogen atom, an optionally substituted hydrocarbon group or an acyl group; or $R^3$ and $R^4$ may be taken together with the adjacent nitrogen atom to form an optionally substituted 4- to 8-membered nitrogen-containing ring, or a salt thereof and thereafter, if necessary, deprotecting the resultant product;

(2) the process described in the above (1), wherein W is at the 5-position on a 2,3-dihydrobenzofuran ring;

(3) the process described in the above (1), which is for producing a compound represented by the formula:

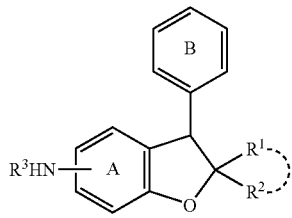

wherein $R^1$ and $R^2$ are the same or different and each is a hydrogen atom, an optionally substituted hydrocarbon group or an optionally substituted heterocyclic group, or $R^1$ and $R^2$ may be taken together with the adjacent carbon atom to form an optionally substituted 3- to 8-membered homocyclic or heterocyclic ring, ring A is a benzene ring that may be optionally substituted in addition to the group represented by $R^3HN$, ring B is an optionally substituted benzene ring, and $R^3$ is (1) a hydrogen atom, (2) an aliphatic hydrocarbon group that is substituted with an optionally substituted aromatic group and may be optionally further substituted or (3) an acyl group containing an optionally substituted aromatic group, or a salt thereof;

(4) the process described in the above (1), wherein a compound represented by the formula:

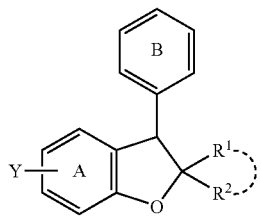

wherein $R^1$ and $R^2$ are the same or different and each is a hydrogen atom, an optionally substituted hydrocarbon group or an optionally substituted heterocyclic group, or $R^1$ and $R^2$ may be taken together with the adjacent carbon atom to form an optionally substituted 3- to 8-membered homocyclic or heterocyclic ring, Y is a halogen atom, ring A is a benzene ring that may be optionally further substituted in addition to the group represented by Y, and ring B is an optionally substituted benzene ring, or a salt thereof is produced by subjecting a compound represent by the formula:

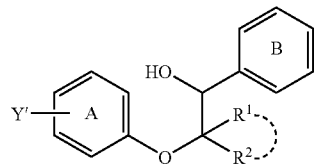

wherein Y' is a hydrogen atom or a halogen atom, ring A is a benzene ring that may be optionally further substituted in addition to the group represented by Y' and other symbols are as defined above, or a salt thereof to ring-closure reaction in the presence of an acid and thereafter, when Y' is a hydrogen atom, halogenating the reaction product;

(5) the process described in the above (4), wherein a compound presented by the formula:

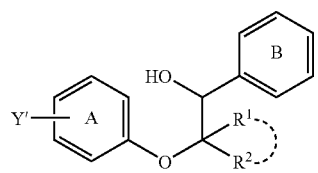

wherein $R^1$ and $R^2$ are the same or different and each is a hydrogen atom, an optionally substituted hydrocarbon group or an optionally substituted heterocyclic ring, or $R^1$ and $R^2$ may be taken together with the adjacent carbon atom to form an optionally substituted 3- to 8-membered homocyclic or heterocyclic ring, Y' is a hydrogen atom or a halogen atom, ring A is a benzene ring that may be optionally further substituted in addition to the group represented by Y', and ring B is an optionally substituted benzene ring, or a salt thereof is produced by subjecting a compound represented by the formula:

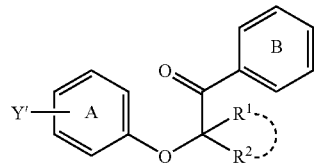

wherein each symbols is as defined above, or a salt thereof to reduction reaction;

(6) the process described in the above (5), wherein a compound represented by the formula:

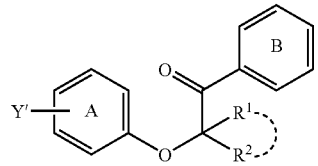

wherein $R^1$ and $R^2$ are the same or different and each is a hydrogen atom, an optionally substituted hydrocarbon group or an optionally substituted heterocyclic group, or $R^1$ and $R^2$ may be taken together with the adjacent carbon atom to form an optionally substituted 3- to 8-membered homocyclic or heterocyclic ring, Y' is a hydrogen atom or a halogen atom, ring A is a benzene ring that may be optionally further substituted in addition to the group represented by Y', and ring B is an optionally substituted benzene ring, or a salt thereof is produced by reacting a compound represented by the formula:

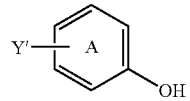

wherein each symbol is as defined above, or a salt thereof with a compound presented by the formula:

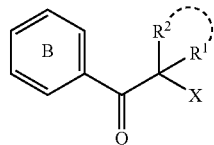

wherein X is a halogen atom or $OSO_2R$ in which R is a $C_{1-6}$ alkyl group or an optionally substituted $C_{6-14}$ aryl group and other symbols are as defined above, or a salt thereof in the presence of a base; and (7) the process described in the above (1), wherein a compound represents by the formula:

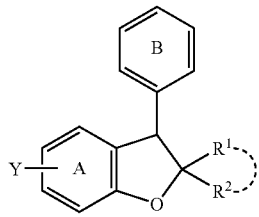

wherein $R^1$ and $R^2$ are the same or different and each is a hydrogen atom, an optionally substituted hydrocarbon group or an optionally substituted heterocyclic group, or $R^1$ and $R^2$ may be taken together with the adjacent carbon atom to form an optionally substituted 3- to 8-membered homocyclic or heterocyclic ring, Y is a halogen atom, ring A is a benzene ring that may be optionally further substituted in addition to the group represented by Y, and ring B is an optionally substituted benzene ring, or a salt thereof is produced by reacting a compound represented by the formula:

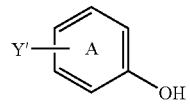

wherein Y' is a hydrogen atom or a halogen atom, ring A is a benzene ring that may be optionally further substituted in addition to the group represented by Y', and other symbols are as defined above, or a salt thereof with a compound represented by the formula:

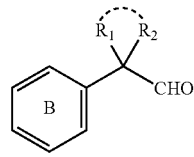

wherein each symbol is as defined above, or a salt thereof in the presence of an acid and thereafter, when Y' is a hydrogen atom, halogenating the reaction the product.

By the process of the present invention, novel compounds:

(8) 2-methyl-1-(4-methylphenyl)-2-(2,3,5-trimethylphenoxy)-1-propanone, (9) 2-methyl-1-(4-methylphenyl)-2-(2,3,5-trimethylphenoxy)-1-propanol,

(10) 5-bromo-2,2,4,6,7-pentamethyl-3-(4-methylphenyl)-2,3-dihydro-1-benzofuran, and

(11) N-benzyl-2,2,4,6,7-pentamethyl-3-(4-methylphenyl)-2,3-dihydro-1-benzofuran-5-amine are obtained. The present invention also provides these novel compounds.

DETAILED EXPLANATION OF THE INVENTION

In the above formulas, examples of the "hydrocarbon group" of "an optionally substituted hydrocarbon group" represented by $R^1$ or $R^2$ include chain or cyclic hydrocarbon groups (e.g., alkyl, alkenyl, alkynyl, cycloalkyl, aryl, etc.). Among them, chain or cyclic hydrocarbon groups having 1 to 16 carbon atoms are preferred.

Examples of "alkyl" include preferably $C_{1-6}$ alkyl (e.g., methyl, ethyl, propyl, isopropyl, butyl, isobutyl, sec-butyl, tert-butyl, pentyl, hexyl etc.).

Examples of "alkenyl" include preferably $C_{2-6}$ alkenyl (e.g., vinyl, allyl, isopropenyl, butenyl, isobutenyl, sec-butenyl etc.).

Examples of "alkynyl" include preferably $C_{2-6}$ alkynyl (e.g., ethynyl, propargyl, butynyl, 1-hexynyl etc.).

Examples of "cycloalkyl" include preferably $C_{3-6}$ cycloalkyl (e.g. cyclopropyl, cyclobutyl, cyclopentyl, cyclohexyl etc.).

Examples of "aryl" include preferably $C_{6-14}$ aryl (e.g., phenyl, 1-naphthyl, 2-naphtyl, biphenylyl, 2-anthryl etc.).

Examples of "substituent(s)" for "an optionally substituted hydrocarbon group" represented by $R^1$ or $R^2$ include (1) a halogen atom (e.g., fluorine, chlorine, bromine, iodine, etc.), (2) $C_{1-3}$ alkylenedioxy (e.g., methylenedioxy, ethylenedioxy etc.), (3) nitro, (4) cyano, (5) optionally halogenated $C_{1-6}$ alkyl, (6) optionally halogenated $C_{2-6}$ alkenyl, (7)

optionally halogenated $C_{2-6}$ alkynyl, (8) optionally halogenated $C_{3-6}$ cycloalkyl, (9) $C_{6-14}$ aryl (e.g., phenyl, 1-naphthyl, 2-naphthyl, biphenylyl, 2-anthryl etc.), (10) optionally halogenated $C_{1-6}$ alkoxy, (11) optionally halogenated $C_{1-6}$ alkylthio or mercapto, (12) hydroxyl, (13) amino, (14) mono-$C_{1-6}$ alkylamino (e.g., methylamino, ethylamino, etc.), (15) mono-$C_{6-14}$ arylamino (e.g., phenylamino, 1-naphthylamino, 2-naphthylamino etc.), (16) di-$C_{1-6}$ alkylamino (e.g. dimethylamino, diethylamino etc.), (17) di-$C_{6-14}$ arylamino (e.g. diphenylamino etc.), (18) acyl, (19) acylamino, (20) acyloxy, (21) optionally substituted 5- to 7-mebered saturated cyclic amino, (22) 5- to 10-memberd aromatic heterocyclic group (e.g., 2- or 3-thienyl, 2-, 3- or 4-pyridyl, 2-, 3-, 4-, 5- or 8-quinolyl, 1-, 3-, 4- or 5-isoquinolyl, 1-, 2- or 3-indolyl, 2-benzothiazolyl, 2-benzo[b]thienyl, benzo[b]furanyl etc.), (23) sulfo, (24) $C_{6-14}$ aryloxy (e.g., phenyloxy, naphthyloxy etc.) and the like.

The "hydrocarbon group" may have 1 to 5, preferably 1 to 3 substituents, for example, those as mentioned above, at any substitutable positions. When 2 or more substituents are present, each of them may be the same or different.

Examples of the above-mentioned "optionally halogenated $C_{1-6}$ alkyl" include $C_{1-6}$ alkyl (e.g., methyl, ethyl, propyl, isopropyl, butyl, isobutyl, sec-butyl, tert-butyl, pentyl, hexyl etc.) that may have 1 to 5, preferably 1 to 3 halogen atoms (e.g., fluorine, chlorine, bromine, iodine etc.). Specific examples thereof include methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl and the like.

Examples of the above-mentioned "optionally halogenated $C_{2-6}$ alkenyl" include $C_{2-6}$ alkenyl (e.g., vinyl, allyl, isopropenyl, butenyl, isobutenyl, sec-butenyl etc.) that may have 1 to 5, preferably 1 to 3 halogen atoms (e.g., fluorine, chlorine, bromine, iodine etc.). Specific examples thereof include vinyl, allyl, isopropenyl, butenyl, isobutenyl, sec-butenyl, 3,3,3-trifluoro-1-propenyl, 4,4,4-trifluoro-1-butenyl and the like.

Examples of the above-mentioned "optionally halogenated $C_{2-6}$ alkynyl" include $C_{2-6}$ alkynyl (e.g., ethynyl, popargyl, butynyl, 1-hexynyl etc.) that may have 1 to 5, preferably 1 to 3 halogen atoms (e.g., fluorine, chlorine, bromine, iodine etc.). Specific examples thereof include ethynyl, propargyl, butynyl, 1-hexynyl, 3,3,3-trifluoro-1-propynyl, 4,4,4-trifluoro-1-butynyl and the like.

Examples of the above-mentioned "optionally halogenated $C_{3-6}$ cycloalkyl" include $C_{3-6}$ cycloalkyl (e.g., cyclopropyl, cyclobutyl, cyclopentyl, cyclohexyl etc.) that may have 1 to 5, preferably 1 to 3 halogen atoms (e.g., fluorine, chlorine, bromine, iodine etc.). Specific examples thereof include cyclopropyl, cyclobutyl, cyclopentyl, cyclohexyl, 4,4-dichlorocyclohexyl, 2,2,3,3-tetrafluorocyclopentyl, 4-chlorocyclohexyl and the like.

Examples of the above-mentioned "optionally halogenated $C_{1-6}$ alkoxy" include $C_{1-6}$ alkoxy (e.g., methoxy, ethoxy, propoxy, isopropoxy, butoxy, isobutoxy, sec-butoxy, pentyloxy, hexyloxy etc.) that may have 1 to 5, preferably 1 to 3 halogen atoms (e.g., fluorine, chlorine, bromine, iodine etc.). Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy and the like.

Examples of the above-mentioned "optionally halogenated $C_{1-6}$ alkylthio" include $C_{1-6}$ alkylthio (e.g., methylthio, ethylthio, propylthio, isopropylthio, butylthio, sec-butylthio, tert-butylthio etc.) that may have 1 to 5, preferably 1 to 3 halogen atoms (e.g. fluorine, chlorine, bromine, iodine etc.). Specific examples thereof include methylthio, difluoromethylthio, trifluoromethylthio, ethylthio, propylthio, isopropylthio, butylthio, 4,4,4-trifluorobutylthio, pentylthio, hexylthio and the like.

Examples of the above-mentioned "acyl" include formyl, carboxy, carbamoyl, $C_{1-6}$alkyl-carbonyl (e.g., acetyl, propionyl etc.), $C_{3-6}$ cycloalkyl-carbonyl (e.g., cyclopropylcarbonyl, cyclopentylcarbonyl, cyclohexylcarbonyl etc.), $C_{1-6}$ alkoxy-carbonyl (e.g., methoxycarbonyl, ethoxycarbonyl, propoxycarbonyl, tert-butoxycarbonyl etc.), $C_{6-14}$ aryl-carbonyl (e.g., benzoyl, 1-naphthoyl, 2-naphthoyl etc.), $C_{7-16}$ aralkyl-carbonyl (e.g., phenylacetyl, phenylpropionyl etc.), $C_{6-14}$ aryloxy-carbonyl (e.g., phenoxycarbonyl etc.), $C_{7-16}$ aralkyloxy-carbonyl (e.g., benzyloxycarbonyl, phenethyloxycarbonyl etc.), 5- or 6-memberd heterocyclic carbonyl (e.g., nicotinoyl, isonicotinoyl, 2-thenoyl, 3-thenoyl, 2-furoyl, 3-furoyl, morpholinocarbonyl, thiomorpholinocarbonyl, piperidinocarbonyl, 1-pyrrolidinylcarbonyl etc.), mono-$C_{1-6}$ alkyl-carbamoyl (e.g., methylcarbamoyl, ethylcarbamoyl etc.), di-$C_{1-6}$ alkyl-carbamoyl (e.g., dimethylcarbamoyl, diethylcarbamoyl, ethylmethylcarbamoyl etc.), $C_{6-14}$ arlycarbamoyl (e.g., phenylcarbamoyl, 1-naphthylcarbamoyl, 2-naphthylcarbamoyl etc.), thiocarbamoyl, 5- or 6-mebered heterocyclic carbamoyl (e.g., 2-pyridylcarbamoyl, 3-pyridylcarbamoyl, 4-pyridylcarbamoyl, 2-thienylcarbamoyl, 3-thienylcarbamoyl etc.), $C_{1-6}$ arkylsulfonyl (e.g., methylsulfonyl, ethylsulfonyl etc.), $C_{6-14}$ arylsulfonyl (e.g., phenylsulfonyl, 1-naphthylsulfonyl, 2-naphthylsulfonyl etc.), $C_{1-6}$ arkylsulfinyl (e.g., methylsulfinyl, ethylsulfinyl etc.), $C_{6-14}$ arylsulfinyl (e.g., phenylsulfinyl, 1-naphthylsulfinyl, 2-naphthylsulfinyl etc.) and the like.

Examples of the above-mentioned "acylamino" include formylamino, $C_{1-6}$ alkyl-carbonylamino (e.g., acetylamino etc.), $C_{6-14}$ aryl-carbonylamino (e.g., phenylcarbonylamino, naphthylcarbonylamino etc.), $C_{1-6}$ alkoxy-carbonylamino (e.g., methoxycarbonylamino, ethoxycarbonylamino, propoxycarbonylamino, butoxycarbonylamino etc.), $C_{1-6}$ alkyl-sulfonylamino (e.g., methylsulfonylamino, ethylsulfonylamino etc.), $C_{6-14}$ arylsulfonylamino (e.g., phenylsulfonylamino, 2-naphthylsulfonylamino, 1-naphthylsulfonylamino etc.) and the like.

Examples of the above-mentioned "acyloxy" include $C_{1-6}$ arkyl-carbonyloxy (e.g., acetoxy, propionyloxy etc.), $C_{6-14}$ aryl-carbonyloxy (e.g., benzoyloxy, naphthylcarbonyloxy etc.), $C_{1-6}$ alkoxy-carbonyloxy (e.g., methoxycarbonyloxy, ethoxycarbonyloxy, propoxycarbonyloxy, butoxycarbonyloxy etc.), mono-$C_{1-6}$ alkyl-carbamoyloxy (e.g., methylcarbamoyloxy, ethylcarbamoyloxy etc.), di-$C_{1-6}$ alkyl-carbamoyloxy (e.g., dimethylcarbamoyloxy, diethylcarbamoyloxy etc.), $C_{6-14}$ aryl-carbamoyloxy (e.g., phenylcarbamoyloxy, naphthylcarbamoyloxy etc.), nicotinoyloxy and the like.

Examples of the "5- to 7-memberd saturated cyclic amino" of the above-mentioned "optionally substituted 5- to 7-memberd saturated cyclic amino" include morpholino, thiomorpholino, piperazin-1-yl, piperidino, pyrrolidin-1-yl and the like. Examples of "substituent(s)" for the "optionally substituted 5- to 7-memberd saturated cyclic amino" include 1 to 3 substituents selected from $C_{1-6}$ alkyl (e.g., methyl, ethyl, propyl, isopropyl, butyl, isobutyl, sec-butyl, tert-butyl, pentyl, hexyl etc.), $C_{6-14}$ aryl (e.g., phenyl, 1-naphthyl, 2-naphthyl, biphenylyl, 2-anthryl etc.), 5- to 10-memberd aromatic heterocyclic groups (e.g., 2- or 3-thienyl, 2-, 3- or 4-pyridyl, 2-, 3-, 4-, 5- or 8-quinolyl, 1-, 3-, 4- or 5-isoquinolyl, 1-, 2- or 3-indolyl, 2-benzothiazolyl, 2-benzo[b]thienyl, benzo[b]furanyl etc.) and the like.

Examples of the "heterocyclic group" of "an optionally substituted heterocyclic group" represented by $R^1$ or $R^2$ include 5- to 14-memberd heterocyclic groups (aromatic heterocyclic groups, saturated or unsaturated non-aromatic heterocyclic groups) containing 1 to 4 heteroatoms selected from a nitrogen atom, a sulfur atom and an oxygen atom in addition to carbon atoms.

Examples of the "aromatic heterocyclic group" include 5- to 14-membered, preferably 5- to 10-membered aromatic heterocyclic groups containing 1 or more (for example, 1 to 4) heteroatoms selected from a nitrogen atom, a sulfur atom and an oxygen atom in addition to carbon atoms. Specific examples thereof include monovalent groups formed by removing an optional hydrogen atom from aromatic heterocyclic rings such as thiophene, benzothiophene, benzofuran, benzimidazole, benzoxazole, benzothiazole, benzisothiazole, naphtho[2,3-b]thiophene, furan, isoindolizine, xantholene, phenoxathiine, pyrrole, imidazole, pyrazole, pyridine, pyrazine, pyrimidine, pyridazine, indole, isoindole, 1H-indazole, purine, 4H-quinolizine, isoquinoline, quinoline, phtharazine, naphthyridine, quinoxaline, quinazoline, cinnoline, carbazole, β-carboline, phenanthridine, acridine, phenazine, thiazole, isothiazole, phenothiazine, oxazole, isoxazole, furazane, phenoxazine and the like, or rings formed by fusing the above rings (preferably monocyclic rings) with 1 to plural (preferably 1 or 2) aromatic rings (e.g. benzene ring etc.).

Preferred examples of the "aromatic heterocyclic group" include 5- or 6-membered aromatic heterocyclic groups that may be fused with one benzene ring. Specific examples thereof include 2-, 3- or 4-pyridyl, 2-, 3-, 4-5- or 8-quinolyl, 1-, 3-, 4- or 5-isoquinolyl, 1-, 2- or 3-indolyl, 2-benzothiazolyl, 2-benzo[b]thienyl, benzo[b]furanyl, 2- or 3-thienyl and the like. More preferable examples include 2- or 3-thienyl, 2-, 3- or 4-pyridyl, 2- or 3-quinolyl, 1-isoquinolyl, 1- or 2-indolyl, 2-benzothiazolyl and the like.

Examples of the "non-aromatic heterocyclic group" include 3- to 8-membered (preferably 5- or 6-membered) saturated or unsaturated (preferably saturated) non-aromatic heterocyclic groups (aliphatic heterocyclic groups) such as oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl and the like.

As "substituent(s)" for "an optionally substituted heterocyclic group" represented by $R^1$ or $R^2$, the same number of the same substituents as the above-mentioned "substituents" for "an optionally substituted hydrocarbon group" represented by $R^1$ or $R^2$ can be used.

Examples of the "3- to 8-membered homocyclic ring" of "an optionally substituted 3- to 8-membered homocyclic ring" formed by $R^1$ and $R^2$ include $C_{3-8}$ cycloalkane such as cyclopropane, cyclobutane, cyclopentane, cyclohexane or the like.

Examples of the "3- to 8-membered heterocyclic ring" of "an optionally substituted 3- to 8-membered heterocyclic ring" formed by $R^1$ and $R^2$ include 3- to 8-membered heterocyclic rings containing 1 to 4 heteroatoms selected from a nitrogen atom, a sulfur atom and an oxygen atom in addition to carbon atoms, such as aziridine, azetidine, morpholine, thiomorpholine, piperazine, piperidine, pyrrolidine, hexamethyleneimine, heptamethyleneimine, hexahydropyrimidine or the like.

As "substituent(s)" for "an optionally substituted 3- to 8-membered homocyclic or heterocyclic ring" formed by $R^1$ and $R^2$, the same number of the same substituents as the above-mentioned "substituents" for "an optionally substituted hydrocarbon group" represented by $R^1$ or $R^2$ can be used.

In the above formulas, Y represents a halogen atom and Y' represents a halogen atom or a hydrogen atom.

Examples of a halogen atom represented by Y and Y' include fluorine, chlorine, bromine, iodine and the like.

In the above formulas, ring A represents a benzene ring that may be optionally further substituted in addition to the substituents (i.e. Y, Y', W and $R^3$HN—) represented by the formulas. The benzene ring may have, as the further "substituent", 1 to 3 (preferably 2 or 3) of the same substituents as the above-mentioned "substituents" for "an optionally substituted hydrocarbon group" represented by $R^1$ or $R^2$ at substitutable positions. When the number of the further substituents is 2 or more, each of the substituents may be the same or different.

Ring B represents an optionally substituted benzene ring. The benzene ring may have, as the substituent, 1 to 3 of the same substituents as the above-mentioned "substituents" for "an optionally substituted hydrocarbon group" represented by $R^1$ or $R^2$ at substitutable positions. When the number of substituents is 2 or more, each of the substituents may be the same or different.

In the above formulas, W represents:

(i) a group represented by the formula:

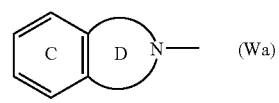

wherein ring C is an optionally substituted benzene ring and ring D is a 5- to 7-membered nitrogen-containing heterocyclic ring that may be optionally substituted with halogen or an optionally substituted hydrocarbon group, or (ii) a group represented by the formula:

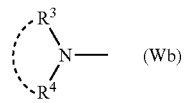

wherein $R^3$ is (1) a hydrogen atom, (2) an aliphatic hydrocarbon group that is substituted with an optionally substituted aromatic group and may be optionally further substituted or (3) an acyl group containing an optionally substituted aromatic group; $R^4$ is a hydrogen atom, an optionally substituted hydrocarbon group or an acyl group, or $R^3$ and $R^4$ may be taken together with the adjacent nitrogen atom to form an optionally substituted 4- to 8-membered ring.

In the formula (Wa), "an optionally substituted benzene ring" represented by ring C may have, as "substituent(s)", 1 to 4 (preferably 1 or 2) of the same substituents as the above-mentioned "substituents" for "an optionally substituted hydrocarbon group" represented by $R^1$ or $R^2$ at substitutable positions. When the number of substituents is 2 or more, each of the substituents may be the same or different.

Examples of "a 5- to 7-membered nitrogen-containing heterocyclic ring" represented by ring D include 5- to 7-membered nitrogen-containing heterocyclic rings such as pyrrole (e.g., 1H-pyrrole etc.), dihydropyrrole (e.g., 2,5-dihydro-1H-pyrrole etc.), dihydropyridine (e.g., 1,2-dihydropyridine etc.), tetrahydropyridine (e.g., 1,2,3,4-tetrahydropyridine etc.), azepine (e.g., 1H-azepine etc.), dihydroazepine (e.g., 2,3-dihydro-1H-azepine, 2,5-dihydro-1H-azepine, 2,7-dihydro-1H-azepine etc.), tetrahydroazepine (e.g., 2,3,6,7-tetrahydro-1H-azepine, 2,3,4,7-tetrahydro-1H-azepine etc.) and the like.

Examples of "halogen" as "substituent(s)" which ring D may have include fluorine, chlorine, bromine, iodine and the like.

Examples of "an optionally substituted hydrocarbon group" as "substituent(s)" which ring D may have include the same groups as the above-mentioned "optionally substituted hydrocarbon group" represented by $R^1$ or $R^2$.

Ring D may have 1 to 3 of the above-mentioned substituents at substitutable positions. When the number of substituents is 2 or more, each of the substituents may be the same or different.

In the formula (Wb), examples of the "aromatic group" of "an optionally substituted aromatic group" as a substituent of "an aliphatic hydrocarbon group that is substituted with an optionally substituted aromatic group and may be optionally further substituted" represented by $R^3$ include an aromatic hydrocarbon group, an aromatic heterocyclic group and the like.

Examples of the "aromatic hydrocarbon group" include monocyclic or fused polycyclic (di- or tricyclic) aromatic hydrocarbon groups having 6 to 14 carbon atoms. Specific examples thereof include $C_{6-14}$ aryl such as phenyl, 1-naphthyl, 2-naphthyl, biphenylyl, anthryl and the like, preferably $C_{6-10}$ aryl such as phenyl, 1-naphthyl, 2-naphthyl and the like.

Examples of the "aromatic heterocyclic group" include 5- to 14-membered, preferably 5- to 10-membered aromatic heterocyclic groups containing 1 or more (for example 1 to 4) heteroatoms selected from a nitrogen atom, a sulfur atom and an oxygen atom in addition to carbon atoms. Specific examples thereof include monovalent groups formed by removing an optional hydrogen atom from aromatic heterocyclic rings such as thiophene, benzothiophene, benzofuran, benzimidazole, benzoxazole, benzothiazole, benzisothiazole, naphtho[2,3-b]thiophene, furan, isoindolizine, xantholene, phenoxathiine, pyrrole, imidazole, pyrazole, pyridine, pyrazine, pyrimidine, pyridazine, indole, isoindole, 1H-indazole, purine, 4H-quinolizine, isoquinoline, quinoline, phtharazine, naphthyridine, quinoxaline, quinazoline, cinnoline, carbazole, β-carboline, phenanthridine, acridine, phenazine, thiazole, isothiazole, phenothiazine, oxazole, isoxazole, furazane, phenoxazine and the like, or rings formed by fusing the above rings (preferably monocyclic rings) with 1 to plural (preferably 1 or 2) aromatic rings (e.g. benzene ring etc.).

Preferred examples of the "aromatic heterocyclic group" include 5- or 6-membered aromatic heterocyclic groups that may be optionally fused with one benzene ring. Specific examples thereof include 2-, 3- or 4-pyridyl, 2-, 3-, 4-, 5- or 8-quinolyl, 1-, 3-, 4- or 5-isoquinolyl, 1-, 2- or 3-indolinyl, 2-benzothiazolyl, 2-benzo[b]thienyl, benzo[b]furanyl, 2- or 3-thienyl and the like. More preferred are 2- or 3-thienyl, 2-, 3- or 4-pyridyl, 2-or 3-quinolyl, 1-isoquinolyl, 1-or 2-indolyl, 2-benzothiazolyl and the like.

As "substituent(s)" for the "optionally substituted aromatic group", the same number of the same substituents as the above-mentioned "substituents" for "an optionally substituted hydrocarbon group" represented by $R^1$ or $R^2$ can be used.

Examples of the "aliphatic hydrocarbon group" of "an aliphatic hydrocarbon group that is substituted with an optionally substituted aromatic group and may be optionally further substituted" represented by $R^3$ include alkyl, alkenyl, alkynyl, cycloalkyl and the like. Among them, $C_{1-10}$ alkyl, $C_{2-10}$ alkenyl, $C_{2-10}$ alkynyl, $C_{3-10}$ cycloalkyl and the like are preferred.

Preferred examples of "alkyl" include $C_{1-6}$ alkyl (e.g., methyl, ethyl, propyl, isopropyl, butyl, isobutyl, sec-butyl, tert-butyl, pentyl, hexyl etc.) and the like.

Preferred examples of "alkenyl" include $C_{2-6}$ alkenyl (e.g., vinyl, allyl, isopropenyl, butenyl, isobutenyl, sec-buteny etc.) and the like.

Preferred examples of "alkynyl" include $C_{2-6}$ alkynyl (e.g., ethynyl, propargyl, butynyl, 1-hexynyl etc.) and the like.

Preferred examples of "cycloalkyl" include $C_{3-6}$ cycloalkyl (e.g., cyclopropyl, cyclobutyl, cyclopentyl, cyclohexyl etc.) and the like.

Among them, $C_{1-6}$ alkyl is preferred.

The "aliphatic hydrocarbon group" has at least one "optionally substituted aromatic group" at a substitutable position. The "aliphatic hydrocarbon group" may have further 1 to 2 "optionally substituted aromatic groups". When the number of the substituents is 2 or more, each of the substituents may be the same or different.

As "substituent(s)" which the "aliphatic hydrocarbon group" may further have, the same number of the same substituents as the above-mentioned "substituents" for "an optionally substituted hydrocarbon groups" represented by $R^1$ or $R^2$ can be used.

As the "acyl group" of "an acyl group containing an optionally substituted aromatic group" represented by $R^3$, the same group as the above-mentioned "acyl group" as "substituent(s)" for "an optionally substituted hydrocarbon group" represented by $R^1$ or $R^2$ can be used.

As the "optionally substituted aromatic group" of "an acyl group containing an optionally substituted aromatic group" represented by $R^3$, the same group as the above-mentioned "optionally substituted aromatic group" of "an aliphatic hydrocarbon group that is substituted with an optionally substituted aromatic group and may be optionally further substituted" represented by $R^3$ can be used.

Preferred specific examples of "an acyl group containing an optionally substituted aromatic group" represented by $R^3$ include $C_{6-14}$ aryl-carbonyl (e.g, benzoyl, 1-naphthoyl, 2-naphthoyl etc.), $C_{7-16}$ aralkyl-carbonyl (e.g., phenylacetyl, phenylpropionyl etc.), $C_{6-14}$ aryloxy-carbonyl (e.g., phenoxycarbonyl etc.), $C_{7-16}$ aralkyloxy-carbonyl (e.g., benzyloxycarbonyl, phenethyloxycarbonyl etc.), 5-or 6-membered heterocyclic carbonyl (e.g., nicotinoyl, isonicotinoyl, 2-thenoyl, 3-thenoyl, 2-furoyl, 3-furoyl, morpholinocarbonyl, thiomorpholinocarbonyl, piperidinocarbonyl, 1-pyrrolidinylcarbonyl etc.), $C_{6-14}$ aryl-carbamoyl (e.g., phenylcarbamoyl, 1-naphthylcarbamoyl, 2-naphthylcarbamoyl etc.), 5- or 6-membered heterocyclic carbamoyl (e.g., 2-pyridylcarbamoyl, 3-pyridylcarbamoyl, 4-pyridylcarbamoyl, 2-thienylcarbamoyl, 3-thienylcarbamoyl etc.), $C_{6-14}$ arylsulfonyl (e.g., phenylsulfonyl, 1-naphthylsulfonyl, 2-naphthylsulfonyl etc.), $C_{6-14}$ arylsulfinyl (e.g., phenylsulfinyl, 1-naphthylsulfinyl, 2-naphthylsulfinyl etc.) and the like.

As "an optionally substituted hydrocarbon group" represented by $R^4$, the same group as the above-mentioned "optionally substituted hydrocarbon group" represented by $R^1$ or $R^2$ can be used. As "an acyl group" represented by $R^4$, the same group as the above-mentioned "acyl group" as "substituent(s)" for "an optionally substituted hydrocarbon group" represented by $R^1$ or $R^2$ can be used.

Examples of the "4- to 8-membered nitrogen-containing ring" of "an optionally substituted 4- to 8-membered nitrogen-containing ring" formed by $R^3$ and $R^4$ together with the adjacent nitrogen atom include 4- to 8-membered nitrogen-containing rings such as azetidine, morpholine, pyrrolidine, hexamethyleneimine, heptamethyleneimine, hexahydropyrimidine, pyrrole (e.g., 1H-pyrrole etc.), dihydropyrrole (e.g., 2, 5-dihydro-1H-pyrrole etc.), dihydropyridine (e.g., 1,2-dihydropyridine etc.), piperidine, piperazine, azepine (e.g., 1H-azepine etc.), dihydroazepine (e.g., 2,3-dihydro-1H-azepine, 2,5-dihydro-1H-azepine, 2,7-dihydro-1H-azepine etc.), tetrahydroazepine (e.g., 2,3,6,7-tetrahydro-1H-azepine, 2,3,4,7-tetrahydro-1H-azepine etc.), pentahydroazepine, 1,4-diazepane and the like.

As "substituent(s)" for "an optionally substituted 4- to 8-membered nitrogen-containing ring" formed by $R^3$ and $R^4$, the same number of the same groups as the above-mentioned "substituents" for "an optionally substituted hydrocarbon group" represented by $R^1$ or $R^2$ can be used.

X represents a halogen atom or $OSO_2R$ wherein R is a $C_{1-6}$ alkyl group or an optionally substituted $C_{6-14}$ aryl group. Examples of a halogen atom include fluorine, chlorine, bromine, iodine and the like. Examples of a $C_{1-6}$alkyl group represented by R include methyl, ethyl, propyl, isopropyl, butyl, isobutyl, sec-butyl, tert-butyl, pentyl, hexyl and the like. Examples of the "$C_{6-14}$ aryl group" of "an optionally substituted $C_{6-14}$ aryl group" represented by R include phenyl, 1-naphthyl, 2-naphthyl, biphenylyl, 2-anthryl and the like. As "substituent(s)" thereof, the same number of the same groups as the above-mentioned "substituents" for "an optionally substituted hydrocarbon group" represented by $R^1$ or $R^2$ can be used.

A salt of compounds represented by the above formulas may be, for example, a metal salt, an ammonium salt or a salt with an organic base when the compounds have an acidic group such as —COOH; or a salt with an inorganic acid, an organic acid, a basic or acidic amino acid, or the like as well as a inner salt when the compounds have a basic group such as —$NH_2$. Preferred examples of a metal salt include alkali metal salts such as a sodium salt, a potassium salt and the like; alkaline earth metal salts such as a calcium salt, magnesium salt, a barium salt and the like; an aluminium salt, and the like. Preferred examples of a salt with an organic base include salts with trimethylamine, triethylamine, pyridine, picoline, ethanolamine, diethanolamine, triethanolamine, dicyclohexylamine, N,N-dibenzylethylenediamine and the like. Preferred examples of a salt with an inorganic acid include salts with hydrochloric acid, hydrobromic acid, nitric acid, sulfuric acid, phosphoric acid and the like. Preferred examples of a salt with an organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like. Preferred examples of a salt with a basic amino acid include salts with arginine, lysine, ornithine and the like. Preferred examples of a salt with an acidic amino acid include salts with aspartic acid, glutamic acid and the like.

Among them, pharmaceutically acceptable salts are preferable. For example, when the compounds have an acidic functional group, examples thereof include inorganic salts such as alkali metal salts (e.g., sodium salt, potassium salt etc.), alkaline earth metal salts (e.g., calcium salt, magnesium salt, barium salt etc.) as well as ammonium salts and the like. When the compounds have a basic functional group, examples thereof include inorganic salts such as hydrochloride, sulfate, phosphate, hydrobromide and the like, and organic salts such as acetate, maleate, fumarate, succinate, methanesulfonate, p-toluenesulfonate, citrate, tartarate and the like.

The process of the present invention is shown by the following Reaction Scheme 1.

Reaction Scheme I
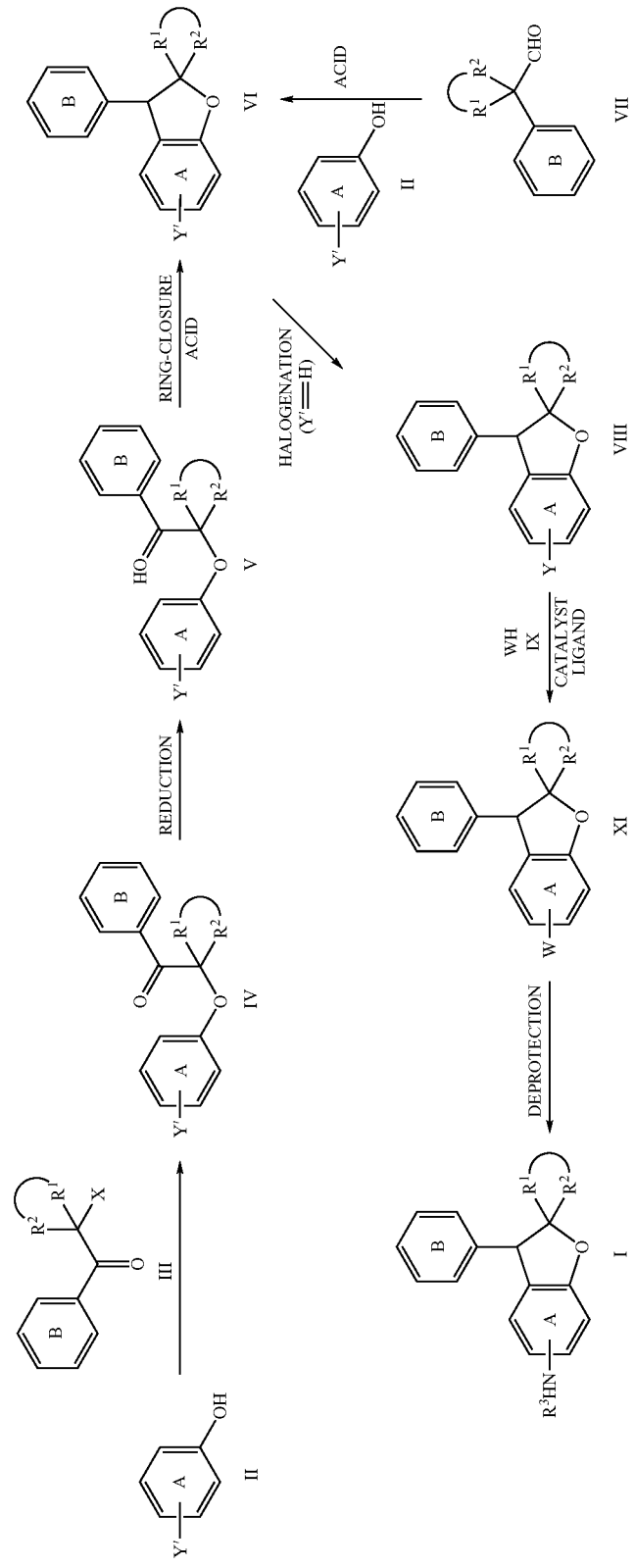

According to the Reaction Scheme 1, first, Compound (IV) is prepared by reacting Compound (II) with Compound (III) in the presence of a base. The reaction is usually performed in a solvent. The solvent may be any solvent as long as the reaction is not inhibited. Examples of such a solvent include alcohols (e.g., methanol, ethanol, propanol, isopropanol, butanol, tert-butanol, methoxyethanol etc.), halogenated hydrocarbons (e.g., dichloromethane, chloroform, 1,2-dichloroethane, 1,1,2,2-tetrachloroethane etc.), aromatic hydrocarbons (e.g., benzene, toluene, xylene, chlorobenzene, dichlorobenzene, nitrobenzene etc.), ethers (e.g., ethyl ether, isopropyl ether, tert-butyl methyl ether, tetrahydrofuran, dioxane etc.), nitriles (e.g., acetonitrile, propionitrile etc.), esters (e.g., methyl acetate, ethyl acetate, ethyl propionate etc.), dimethylformamide, dimethylacetamide, N-methylpyrrolidone, dimethyl sulfoxide, hexamethylphosphoramide and the like. These solvents may be used by mixing two or more of them at a convenient ratio.

Examples of the base include tertiary amines (e.g., trimethylamine, triethylamine, tributylamine, N-ethyldiisopropylamine, N-methylmorpholine, DBU (1,8-diazabicyclo[5.4.0]-7-undecene), DBN (1,5-diazabicyclo[4.3.0]-5-nonene) etc.), aromatic amines (e.g., pyridine, picoline, quinoline, N,N-dimethylaniline etc.), alkali metal carbonates (e,g,. sodium hydrogencarbonate, potassium carbonate, sodium carbonate, cesium carbonate etc.), alkali metal hydroxides (e.g., potassium hydroxide, sodium hydroxide, calcium hydroxide etc.) and the like.

The amounts of Compound (III) and a base to be used are 1 to 10 equivalents, preferably 1 to 5 equivalents, for 1 equivalent of Compound (II).

The reaction temperature is usually −20 to 150° C., preferably −10 to 100° C. The reaction time is usually 30 minutes to 24 hours, preferably 1 hour to 24 hours.

Then, Compound (IV) is subjected to reduction reaction to prepare Compound (V).

Examples of a reducing agent used in the reduction reaction include metal hydrides (e.g., aluminum hydride, diisobutylaluminum hydride, tributyltin hydride, triethylsilane etc.), metal hydrogen complex compounds (e.g., lithium aluminum hydride, sodium borohydride, lithium borohydride, bis(2-methoxyethoxy)aluminum sodium hydride, sodium cyanoborohydride etc.), diborane and the like.

The reduction reaction is usually performed in a solvent. The solvent may be any solvent as long as the reaction is not inhibited. Examples of such a solvent include alcohols (e.g., methanol, ethanol, propanol, isopropanol, butanol, tert-butanol, methoxyethanol etc.), halogenated hydrocarbons (e.g., dichloromethane, chloroform, 1,2-dichloroethane, 1,1,2,2-tetrachloroethane etc.), aromatic hydrocarbons (e.g., benzene, toluene, xylene etc.), ethers (e.g., ethyl ether, isopropyl ether, tert-butyl methyl ether, tetrahydrofuran, dioxane etc.), dimethylformamide, dimethylacetamide, N-methylpyrrolidone, dimethyl sulfoxide, hexamethylphosphoramide and the like. These solvents may be used by mixing two or more of them at a convenient ratio.

The amount of a reducing agent to be used is 0.5 to 10 equivalents, preferably 1 to 5 equivalents, for 1 equivalent of Compound (IV).

The reaction temperature is usually −50 to 150° C., preferably −10 to 100° C.

The reaction time is usually 15 minutes to 24 hours, preferably 0.5 hour to 15 hours.

The reduction reaction may be also attained by hydrogenation (catalytic reduction) using a catalyst. Examples of a catalyst used in the catalytic reduction include Raney nickel, platinum oxide, platinum black, platinum carbon, palladium chloride, palladium black, palladium carbon and the like.

The amount of a catalyst to be used is 0.01 to 200%, preferably 0.05 to 100% based on the weight of Compound (IV).

The Hydrogenation is usually performed under a pressure of normal pressure to 20 MPa, preferably normal pressure to 10 MPa.

The hydrogenation reaction is usually performed in a solvent. The solvent may be any solvent as long as the reaction is not inhibited. Examples of such a solvent include alcohols (e.g., methanol, ethanol, propanol, isopropanol, butanol, tert-butanol, methoxyethanol etc.), halogenated hydrocarbons (e.g., dichloromethane, chloroform, 1,2-dichloroethane, 1,1,2,2-tetrachloroethane etc.), aromatic hydrocarbons (e.g., benzene, toluene, xylene etc.), ethers (e.g., ethyl ether, isopropyl ether, tert-butyl methyl ether, tetrahydrofuran, dioxane etc.), dimethylformamide, dimethylacetamide, N-methylpyrrolidone and the like. These solvents may be used by mixing two or more of them at a convenient ratio.

The reaction temperature is usually 0 to 150° C., preferably 10 to 100° C.

The reaction time is usually 15 minutes to 24 hours, preferably 0.5 hour to 15 hours.

Then, Compound (V) is subjected to ring-closure reaction in the presence of an acid to prepare Compound (VI). Examples of an acid used in the ring-closure reaction include mineral acids (e.g., hydrochloric acid, hydrobromic acid, sulfuric acid, phosphoric acid etc.), organic acids (e.g., formic acid, acetic acid, propionic acid, butyric acid, methanesulfonic acid, trichloromethanesulfonic acid, trifluoromethanesulfonic acid, ethanesulfonic acid, benzenesulfonic acid, toluenesulfonic acid, camphorsulfonic acid etc.), Lewis acids (e.g., aluminum chloride, zinc chloride, tin chloride, iron chloride, titanium chloride, boron trifluoride, boron tribromide etc.), strong acidic resins (e.g., Dowex 50, Amberlite IR 120 etc.), polyphosphoric acid, polyphosphoric acid ester and the like.

The ring-closure reaction is usually performed in a solvent. The solvent may be any solvent as long as the reaction is not inhibited. Examples of such a solvent include alcohols (e.g., methanol, ethanol, propanol, isopropanol, butanol, tert-butanol, methoxyethanol etc.), halogenated hydrocarbons (e.g., dichloromethane, chloroform, 1,2-dichloroethane, 1,1,2,2-tetrachloroethane etc.), aromatic hydrocarbons (e.g., benzene, toluene, xylene, chlorobenzene, dichlorobenzene, nitrobenzene etc.), ethers (e.g., ethyl ether, isopropyl ether, tert-butyl methyl ether, tetrahydrofuran, dioxane etc.), nitrites (e.g., acetonitrile, propionitrile etc.), esters (e.g., methyl acetate, ethyl acetate, ethyl propionate etc.), dimethylformamide, dimethylacetamide, N-methylpyrrolidone, dimethyl sulfoxide, hexamethylphosphoramide and the like. These solvents may be used by mixing two or more of them at a convenient ratio. An acid used may be also used as a solvent.

The amount of an acid to be used is 0.1 to 10 equivalents, preferably 1 to 5 equivalents, for 1 equivalent of Compound (V).

The reaction temperature is usually −50 to 150° C., preferably −30 to 100° C.

The reaction time is usually 30 minutes to 24 hours, preferably 1 hour to 15 hours.

Compound (VI) may be also prepared by a reaction of Compound (II) with Compound (VII). The conditions for preparation of Compound (VI) by ring-closure of Compound (V), without changing, can be applied to the reaction of Compound (II) with Compound (VII).

Compound (VI) wherein Y' is a halogen atom corresponds to Compound (VIII) and can be reacted directly with (IX). Compound (VI) wherein Y' is a hydrogen atom is halogenated to prepare Compound (VIII).

Examples of halogen used in the halogenation include chlorine, bromine and iodine. In the halogenation, N-chlorosuccinic imide (NCS), N-bromosuccinic imide (NBS), halogenated amides such as N-bromoacetic amide, sulfuryl chloride and the like may be also used.

The halogenation reaction is usually performed in a solvent. The solvent may be any solvent as long as the reaction is not inhibited. Examples of such a solvent include alcohols (e.g., methanol, ethanol, propanol, isopropanol, butanol, tert-butanol, methoxyethanol etc.), halogenated hydrocarbons (e.g., dichloromethane, chloroform, 1,2-dichloroethane, 1,1,2,2-tetrachloroethane etc.), aromatic hydrocarbons (e.g., benzene, toluene, xylene, chlorobenzene, dichlorobenzene, nitrobenzene etc.), ethers (e.g., ethyl ether, isopropyl ether, tert-butyl methyl ether, tetrahydrofuran, dioxane etc.), nitriles (e.g., acetonitrile, propionitrile etc.), esters (e.g., methyl acetate, ethyl acetate, ethyl propionate etc.), dimethylformamide, dimethylacetamide, N-methylpyrrolidone, dimethyl sulfoxide, hexamethylphosphoramide and the like. These solvents may be used by mixing two or more of them at a convenient ratio.

An organic acid such as formic acid, acetic acid, propionic acid or butyric acid may be also used as a solvent.

The halogenation reaction may be also performed, optionally, in the presence of a base as a deacidifying agent. Examples of such a base include tertiary amines (e.g., trimethylamine, triethylamine, tributylamine, N-ethyldiisopropylamine, N-methylmorpholine, DBU (1,8-diazabicyclo[5.4.0]-7-undecene), DBN (1,5-diazabicyclo[4.3.0]-5-nonene etc.), aromatic amines (e.g., pyridine, picoline, quinoline, N,N-dimethylaniline etc.), alkali metal carbonates (e.g., sodium hydrogencarbonate, potassium carbonate, sodium carbonate, cesium carbonate etc.), alkali metal hydroxides (e.g., potassium hydroxide, sodium hydroxide, calcium hydroxide etc.), organic acid alkali metal salts (e.g., sodium formate, potassium formate, sodium acetate, potassium acetate, sodium propionate, potassium propionate etc.) and the like.

The amounts of a halogenating reagent and a base to be used are 1 to 10 equivalents, preferably 1 to 5 equivalents, for 1 equivalent of Compound (VI).

The reaction temperature is usually −20 to 150° C., preferably 0 to 100° C.

The reaction time is usually 30 minutes to 24 hours, preferably 1 hour to 15 hours.

Then, Compound (XI) is prepared by reacting Compound (VIII) with Compound (IX) in the presence of a catalyst and optionally a ligand. The reaction may be performed by the following method or according to the method described, for example, in Chemistry Letters, 1983, pp. 927-928.

Examples of a catalyst used in the reaction include transition metal compounds (e.g., tris(dibenzylidene)dipalladium, bis(dibenzylidene)palladium, palladium acetate, palladium carbon, palladium chloride, tetrakis(triphenylphosphine)palladium, bis(acetylacetone)nickel, dichlorobis(triphenylphosphine)nickel, bis(1,5-cyclooctadiene)nickel, bis(1,10-phenanthroline)nickel, dichlorobis(1,10-phenanthroline), Raney nickel and the like.

Examples of the ligand include trimethylphosphine, triethylphosphine, tripropylphosphine, triisopropylphosphine, tributylphosphine, tri-tert-butylphosphine, tricyclohexylphosphine, trimethylphosphite, triethylphosphite, tripropylphosphite, triisopropylphosphite, tributylphosphite, tricyclohexylphosphite, triphenylphosphine, tri(o-tolyl)phosphine, 2,2'-bis(diphenylphosphino)-1,1'-dinaphthyl (hereinafter, referred to as BINAP), 1,2-bis(dimethylphosphino)ethane, 1,2-bis(diethylphosphino)ethane, 1,2-bis(dibutylphosphino)ethane, 1,2-bis(dipropylphosphino)ethane, 1,2-bis(diisopropylphosphino)ethane, 1,2-bis(dicyclohexylphosphino)ethane, 1,3-bis(dicyclohexylphosphino)propane, 1,3-bis(diisopropylphosphino)propane, 1,4-bis(diisopropylphosphino)butane, 2,4-bis(dicyclohexylphosphino)pentane, 2-(N,N-dimethylamino)-2'-(dicyclohexylphosphino)biphenyl, 2-(di-tert-butylphosphino)biphenyl, 2-(dicyclohexylphosphino)biphenyl, 2,2'-bis(dicyclohexylphosphino)-1,1'-binaphthyl and the like. Among them, in particular, BINAP, tri-tert-butylphosphine and the like are particularly advantageously used.

The reaction is usually performed in a solvent. The solvent may be any solvent as long as the reaction is not inhibited. Examples of such a solvent include alcohols (e.g., methanol, ethanol, propanol, isopropanol, butanol, tert-butanol, methoxyethanol etc.), halogenated hydrocarbons (e.g., dichloromethane, chloroform, 1,2-dichloroethane, 1,1,2,2-tetrachloroethane etc.), aromatic hydrocarbons (e.g., benzene, toluene, xylene, chlorobenzene, dichlorobenzene, nitrobenzene etc.), ethers (e.g., ethyl ether, isopropyl ether, tert-butyl methyl ether, tetrahydrofuran, dioxane etc.), nitrites (e.g., acetonitrile, propionitrile etc.), esters (e.g., methyl acetate, ethyl acetate, ethyl propionate etc.), dimethylformamide, dimethylacetamide, N-methylpyrrolidone, dimethyl sulfoxide, hexamethylphosphoramide and the like. These solvents may be used by mixing two or more of them at a convenient ratio.

The amount of Compound (IX) to be used is 1 to 10 equivalents, preferably 1 to 5 equivalents, for 1 equivalent of Compound (VIII).

The amount of a catalyst to be used is 0.01 to 10 mol %, preferably 0.1 to 5 mol %, for 1 mol of Compound (VIII).

The amount of a ligand to be used is 0.01 to 20mol %, preferably 0.1 to 10 mol %, for 1 mol of Compound (VIII).

The reaction temperature is −20 to 150° C., preferably 0 to 100° C.

The reaction time is usually 30 minutes to 24 hours, preferably 1 hour to 15 hours.

Then, if W is Wb in Compound (XI), the Compound (XI) is, if necessary, subjected to deprotection (removal of $R^3$ and/or $R^4$ other than a hydrogen atom) to prepare Compound (I).

This deprotection of an amino group is performed by a method known per se or a similar method. The deprotection varies depending on the type of a protecting group ($R^3$ and/or $R^4$) for an amino group. For example, the deprotection is attained by hydrolysis with acid or alkali when a protecting group is an acyl group or by hydrogenolysis when a protecting group is a substituted benzyl group. A solvent used in hydrolysis reaction may be any solvent as long as the reaction is not inhibited. Examples of such a solvent include alcohols (e.g., methanol, ethanol, propanol, isopropanol, butanol, tert-butanol, methoxyethanol etc.), ethers (e.g., ethyl ether, isopropyl ether, tert-butyl methyl ether, tetrahydrofuran, dioxane etc.), dimethylformamide, dimethylacetamide, N-methylpyrrolidone, dimethyl sulfoxide, hexamethylphosphoramide and the like. These solvents may be used by mixing two or more of them at a convenient ratio. The amounts of an acid and an alkali to be used are 1 to 500 equivalents, preferably 1 to 300 equivalents, for 1 mol of Compound (XI).

The reaction temperature is usually −20 to 150° C., preferably 0 to 100° C.

The reaction time is usually 30 minutes to 24 hours, preferably 1 hour to 15 hours.

When hydrogenolysis is performed, the conditions (reaction solvent, reaction temperature, reaction time, catalyst etc.) of catalytic reduction used for preparing Compound (V), without changing, can be applied to the hydrogenolysis.

In the process of the present invention, products obtained in respective steps may be used as a reaction solution or as a crude product in the next reaction. Alternatively, the products may be isolated from a reaction mixture according to a conventional method, and can be easily purified by a conventional separating means (e.g., recrystallization, distillation, chromatography etc.).

In addition, Compound (II), Compound (III) and Compound (VII) used as starting material are known, or can be prepared by a method known per se or the methods shown in Examples described below. For example, Compound (VII) may be prepared by the method described in Helv. Chim. Acta, 54, 968(1971) (H. Kuertzel, et al.).

Compound (XII) can be prepared from the resulting Compound (I) according to the following Reaction Scheme 2.

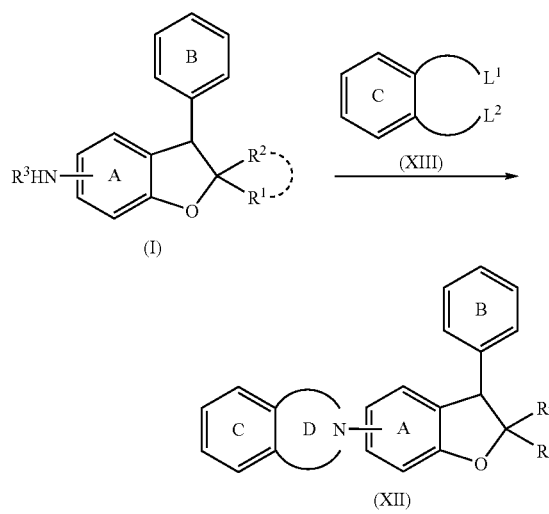

That is, Compound (XII) can be prepared by reacting Compound (Ia) that is Compound (I) wherein $R^3$ is hydrogen with Compound (XIII) represented by the formula:

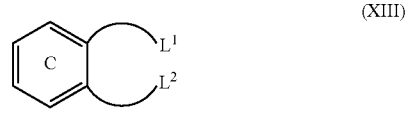

wherein $L^1$ and $L^2$ are leaving groups and ring C is as defined above, optionally in the presence of a base.

Examples of "leaving groups" represented by $L^1$ and $L^2$ include hydroxyl, halogen atoms (e.g., fluorine, chlorine, bromine, iodine etc.), optionally halogenated $C_{1-5}$ alkylsulfonyloxy (e.g., methanesulfonyloxy, ethanesulfonyloxy, trichloromethanesulfonyloxy etc.), optionally substituted $C_{6-10}$ arylsulfonyloxy and the like. Examples of "optionally substituted $C_{6-10}$ arylsulfonyloxy" include $C_{6-10}$ arylsulfonyloxy (e.g., phenylsulfonyloxy, naphthylsulfonyloxy etc.) that may be optionally substituted with 1 to 3 substituents selected from $C_{1-6}$ alkyl (e.g., methyl, ethyl, propyl, isopropyl, butyl, isobutyl, sec-butyl, tert-butyl, pentyl, hexyl etc.), $C_{1-6}$ alkoxy (e.g., methoxy, ethoxy, propoxy, isopropoxy, butoxy, isobutoxy, sec-butoxy, pentyloxy, hexyloxy etc.) and nitro. Specific examples thereof include benzenesulfonyloxy, m-nitrobenzenesulfonyloxy, p-toluenesulfonyloxy and the like.

Compound (XIII) is a compound that is capable of forming, together with the amino group substituted on ring A of Compound (I), a group represented by the formula:

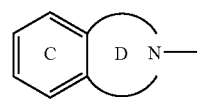

wherein each symbol is as defined above. For example, as Compound (XIII), a compound represented by the formula:

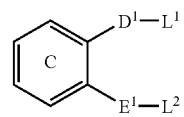

wherein $D^1$ is a group represented by the formula —$(CH_2)$ $d^1$- ($d^1$ is an integer of 0 to 3) that may be optionally substituted with halogen or an optionally substituted hydrocarbon group, $E^1$ is a group represented by the formula —$(CH_2)e^1$- ($e^1$ is an integer of 0 to 3) that may be optionally substituted with halogen or an optionally substituted hydrocarbon group, the sum of $d^1$ and $e^1$ is an integer of 2 to 4, and $L^1$ and $L^2$ are as defined above, is used.

As the halogen and the optionally substituted hydrocarbon group, the same halogen and optionally substituted hydrocarbon group as the above-mentioned halogen and optionally substituted hydrocarbon group exemplified as a substituent for a 5- to 7-membered nitrogen-containing heterocyclic ring represented by ring D can be used.

The amount of Compound (XIII) to be used is about 1.0 to about 5.0 mol, preferably about 1.0 to about 2.0 mol, for 1 mol of Compound (I).

Examples of the "base" include basic salts such as sodium carbonate, potassium carbonate, cesium carbonate, sodium hydrogen carbonate and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, alkali metal hydrides such as sodium hydride, potassium hydride and the like, metal amides such as sodium amide, lithium diisopropylamide, lithium hexamethyldisilazide and the like, metal alkoxides such as sodium methoxide, sodium ethoxide, potassium tert-butoxide and the like, and the like.

The amount of a base to be used is about 1.0 to about 10.0 mol, preferably about 2.0 to about 5.0 mol, for 1 mol of Compound (I). Compound (II) may be also prepared by the reaction in the presence of, optionally, a quaternary ammonium salt together with a base.

Examples of the "quaternary ammonium salt" include tetrabutylammonium iodide and the like.

The amount of a quaternary ammonium salt is about 0.1 to about 2.0 mol, preferably about 0.5 to about 1.0 mol, for 1 mol of Compound (I).

The reaction is advantageously performed in a solvent inert to the reaction. Such a solvent is not particularly limited as long as a reaction proceeds. Preferred examples of the solvent include alcohols such as methanol, ethanol, propanol and the like, ethers such as diethyl ether, tetrahydrofuran, dioxane, 1,2-dimethoxyethane and the like, hydrocarbons such as benzene, toluene, cyclohexane, hexane and the like, amides such as N,N-dimethylformamide, N,N-dimethylacetamide and the like, halogenated hydrocarbons such as dichloromethane, chloroform, carbon tetrachloride, 1,2-dichloroethane and the like, nitriles such as acetonitrile, propionitrile and the like, and sulfoxides such as dimethyl sulfoxide and the like, and mixed solvents thereof.

The reaction time is usually about 30 minutes to about 48 hours, preferably about 1 hour to about 24 hours. The reaction temperature is usually about −20 to about 200° C., preferably about 0 to about 150° C.

In place of the above-mentioned reaction, Mitsunobu reaction (Synthesis, 1981, pp. 1-27) may be used.

In the Mitsunobu reaction, Compound (I) and Compound (XIII) wherein $L^1$ and $L^2$ are OH are reacted in the presence of azodicarboxylates (e.g., diethylazodicarboxylate etc.) and phosphines (e.g., triphenylphosphine, tributylphosphine etc.).

The amount of Compound (XIIIa) wherein $L^1$ and $L^2$ are OH to be used is about 1.0 to about 5.0 mol, preferably about 1.0 to about 2.0 mol, for 1 mol of Compound (I).

The amounts of the "azodicarboxylates" and "phosphines" to be used are about 1.0 to about 5.0 mol, preferably about 1.0 to about 2.0 mol, for 1 mol of Compound (I).

This reaction is advantageously performed in a solvent inert to the reaction. Such a solvent is not particularly limited as long as the reaction proceeds. Preferred examples of the solvent include ethers such as diethyl ether, tetrahydrofuran, dioxane, 1,2-dimethoxyethane and the like, hydrocarbons such as benzene, toluene, cyclohexane, hexane and the like, amides such as N,N-dimethylformamide, N,N-dimethylacetamide and the like, halogenated hydrocarbons such as dichloromethane, chloroform, carbon tetrachloride, 1,2-dichloroethane and the like, nitriles such as acetonitrile, propionitrile and the like, and sulfoxides such as dimethyl sulfoxide and the like, and mixed solvents thereof.

The reaction time is usually about 5 minutes to 48 hours, preferably about 30 minutes to about 24 hours. The reaction temperature is usually about −20 to about 200° C., preferably about 0 to about 100° C.

The process of the present invention is suitable for introducing a group represented by W into the 5-position of a 2,3-dihydrobenzofuran ring, depending on substituents present on ring A and ring C. In addition, the above-mentioned process of Reaction Scheme 2 is suitable for preparing optically active Compound (XII) from optically active Compound (I) as starting material because optical resolution of Compound (I) is easy.

For example, optically active form of Compound (Ia), which is Compound (I) wherein $R^3$ is hydrogen, or a salt thereof can be prepared by optical resolution by derivatizing Compound (Ia) into a salt with an optically active acidic compound.

Optical resolution of an optical isomer-mixture (Ia) of a 2,3-dihydrobenzofuran derivative using an optically active acidic compound can be performed, for example, according to the following procedures.

First, in a suitable solvent, diastereomer salts are formed by reacting Compound (Ia) with an optically active acidic compound, an acidic resolution reagent. Examples of an optically active acidic compound include optically active tartaric acid derivatives such as an optically active O, O'-di-acyltartaric acid derivative, optically active amino acid derivatives such as optically active N-acylamino acid, and optically active phosphoric acid derivatives represented by the formula:

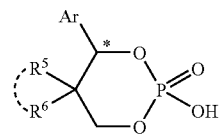

(XIV)

wherein Ar is an optionally substituted aromatic hydrocarbon group, $R^5$ and $R^6$ are each a hydrogen atom, an optionally substituted lower alkyl group, an optionally substituted lower alkoxy group, a halogen atom or a nitro group, or $R^5$ and $R^6$ may be taken together to represent an optionally substituted alkylene group or optionally substituted methylenedioxy, and * symbol represents the position of an asymmetric carbon.

Preferred examples of the acyl group of an O, O'-di-acyltartaric acid derivative include lower ($C_{1-6}$)alkanoyl groups such as acetyl, propionyl, butyryl, valeryl and the like, and aroyl groups such as benzoyl, p-chlorobenzoyl, naphthoyl and the like. Most preferable O, O'-di-acyltartaric acid is O, O'-di-(p-toluoyl) tartaric acid.

Preferred examples of the N-acyl group of a N-acylamino acid derivative include lower ($C_{1-6}$)alkanoyl groups such as acetyl, propionyl, butyryl, valeryl and the like, and an aroyl group such as benzoyl, p-chlorobenzoyl, naphthoyl and the like. Examples of the amino acid include α-phenylglycine. Most preferable N-acylamino acid derivative is N-(3,5-dinitrobenzoyl)-α-phenylglycine.

An optically active phosphoric acid derivative represented by the formula (XIV) can be easily obtained according to the method described in JP-A 61-103886, J. Org. Chem., 50, 4508 (1985) and the like, or some compounds can be easily obtained as a commercially available product. Specific examples thereof include 2-hydroxy-5,5-dimethyl-4-phenyl-1,3,2-dioxaphosphorinane 2-oxide, 4-(2-chlorophenyl)-2-hydroxy-5,5-dimethyl-1,3,2-dioxaphosphorinane 2-oxide, 4-(2,4-dichlorophenyl)-2-hydroxy-5,5-dimethyl-1,3,2-dioxaphosphorinane 2-oxide, 2-hydroxy-4-(2-methoxyphenyl)-5,5-dimethyl-1,3,2-dioxaphosphorinane 2-oxide, and 2-hydroxy-5 5-dimethyl-4-(1-naphthyl)-1,3,2-dioxaphosphorinane 2-oxide.

Examples of the "aromatic hydrocarbon group" of "an optionally substituted aromatic hydrocarbon group" represented by Ar include $C_{6-14}$ aryls (e.g., phenyl, naphthyl etc.). As "substituent(s)" for the "optionally substituted aromatic hydrocarbon group", the same number of the same substituents as the above-mentioned "substituents" for "an optionally substituted hydrocarbon group" represented by $R^1$ or $R^2$ can be used. Preferred examples of the "substituent(s)" include 1 to 2 selected from $C_{1-6}$ alkyl groups such as methyl and ethyl, $C_{1-6}$ alkoxy groups such as methoxy and ethoxy, and halogen atoms such as fluorine chlorine and bromine.

Examples of the "lower alkyl group" of "an optionally substituted lower alkyl group" represented by $R^5$ and $R^6$ include $C_{1-6}$ alkyl (e.g., methyl, ethyl, propyl, isopropyl, butyl, isobutyl, sec-butyl, tert-butyl, pentyl, hexyl etc.). As the "substituent" for the "optionally substituted lower alkyl group", the same number of the same substituents as the above-mentioned "substituents" for "an optionally substituted hydrocarbon group" represented by $R^1$ or $R^2$ can be used. Preferred examples of the "substituent" include 1 to 2 selected from halogen atoms (e.g., fluorine, chlorine, bromine etc.), nitro, cyano, $C_{1-4}$ alkanoyl (e.g., acetyl, propionyl etc.), carboxyl, $C_{1-4}$ alkoxy (e.g., methoxy, ethoxy, propoxy etc.), $C_{1-4}$ alkoxy-carbonyl (e.g., methoxycarbonyl, ethoxycarbonyl, butoxycarbonyl etc.), carbamoyl, and $C_{1-4}$ alkoxy-carbonylamino (e.g., methoxycarbonylamino, ethoxycarbonylamino etc.).

Examples of the "lower alkoxy group" of "an optionally substituted lower alkoxy group" represented by $R^5$ and $R^6$ include $C_{1-6}$ alkoxy (e.g., methoxy, ethoxy, propoxy, isopropoxy, butoxy, isobutoxy, sec-butoxy, pentyloxy, hexyloxy etc.). As "substituent(s)" for the "optionally substituted lower alkoxy group", the same number of the same substitutes as the above-mentioned "substituents" for "an optionally substituted hydrocarbon group" represented by $R^1$ or $R^2$ can be used. Preferred examples of the "substituent(s)" include 1 to 2 selected from $C_{1-4}$ alkanoyl (e.g., acetyl, propionyl etc.), carboxyl, a hydroxyl group, $C_{1-4}$ alkoxy (e.g., methoxy, ethoxy, propoxy etc.) and $C_{1-4}$ alkoxy-carbonyl (e.g., methoxycarbonyl, ethoxycarbonyl, butoxycarbonyl etc.).

Examples of the "halogen atom" represented by $R^5$ and $R^6$ include fluorine, chlorine, bromine, iodine and the like.

When $R^5$ and $R^6$ are taken together to represent an optionally substituted alkylene group, the optionally substituted alkylene group may be unsubstituted alkylene (dimethylene, trimethylene, tetramethylene, pentamethylene) having 2 to 6 carbon atoms or alkylene having 2 to 6 carbon atoms that is substituted with 1 or 2 substituents selected from a lower alkyl group (e.g., $C_{1-4}$ alkyl such as methyl, ethyl, propyl etc.), a lower alkoxy group (e.g., $C_{1-4}$ alkoxy such as methoxy, ethoxy, propoxy etc.), a nitro group and a halogen atom (e.g., fluorine, chlorine, bromine, iodine) at optional positions.

When $R^5$ and $R^6$ are taken together to represent an optionally substituted methylenedioxy group, the methylene may be substituted, for example, with a halogen atom (e.g., fluorine, chlorine, bromine, iodine) or a nitro group.

Preferred examples of $R^5$ and $R^6$ include the case where both of $R^5$ and $R^6$ are a methyl group and the case where $R^5$ and $R^6$ are taken together to represent a tetramethylene group.

Among optically active phosphoric acid derivatives represented by the formula (XIV), most preferred is 2-hydroxy-5,5-dimethyl-4-(1-naphthyl)-1,3,2-dioxaphosphorinane 2-oxide.

Herein, the amount of an acidic resolution reagent to be used is 0.1 to 4-fold mol, preferably 0.6 to 2.5-fold mol, for 1 mol of (Ia). At that time, mineral acid such as hydrochloric acid, sulfuric acid and phosphoric acid, organic acid such as acetic acid, propionic acid, fumaric acid and maleic acid may be also present in such amount that the above molar ratio is attained in terms of the sum of acid and a resolution reagent.

Preferably, a solvent to be used does not chemically change Compound (Ia) and an acidic resolution reagent, and hardly dissolves one of produced diastereomer salts. Examples thereof include water, alcohols such as methanol, ethanol, isopropanol and the like, ethers such as diethyl ether, diisopropyl ether, 1,2-dimethoxyethane, tetrahydrofuran, tetrahydropyran and the like, ketones such as acetone, 2-butanone and the like, nitrites such as acetonitrile and the like, and aromatic hydrocarbons such as benzene and toluene. These may be used alone or by mixing two or more of these. The amount of a solvent to be used is usually 1 to 1000-fold, preferably 1 to 100-fold, based on the amount of Compound (Ia). The temperature is usually 15° C. to a boiling point of a solvent used.

After formation of diastereomer salts, one of the salts can be crystallized by cooling or concentration. Depending on conditions, a hardly soluble salt may be easily crystallized by allowing to stand or stir at room temperature without procedures such as cooling and concentration.

The crystallized salt can be easily separated by a conventional solid-liquid separation method such as centrifugation. In addition, the purity of a crystal of the separated salt can be increased by a method known per se such as recrystallization, if necessary.

The mother liquor after separation of a hardly soluble salt, as it is, contains only easily soluble salts in some cases. Easily soluble salts can be separated directly from the mother liquor or can be separated by concentration of the mother liquor followed by cooling.

For degradation of the salts thus obtained, any of known methods may be used. For example, the objective can be attained by treatment of the salts with an alkali or an acid. Usually, the salts are treated with a water-soluble base such as aqueous sodium hydroxide solution or an aqueous sodium hydrogen carbonate solution to release an optically active 2,3-dihydrobenzofuran compound, and then the optically active compound can be isolated, for example, by a solid-liquid separation method such as filtration or centrifugation, or by extraction procedure with an organic solvent. Base treatment is usually performed at around −10 to 25° C. The amount of a base to be used is 1 to 5 mol-fold based on 1 mol of a diastereomer salt. The concentration of such a base is 1 to 50% by weight, preferably 5 to 20% by weight.

The basic aqueous layer after separation of the optically active 2,3-dihydrobenzofuran compound can be acidified using acid such as hydrochloric acid and sulfuric acid to recover a resolution reagent, and the resolution reagent can be used again.

The optically active 2,3-dihydrobenzofuran compound thus obtained may be used as a reaction solution or as a crude product in the next reaction, but may be purified by conventional separation means (e.g., recrystallization, distillation, chromatography etc.), which may be used thereafter.

The resulting Compounds (I), (XI) and (XII) are low toxic, have the excellent pharmaceutical activities such as neurotrophic factor-like activity, neurotrophic factor activity-enhancing activity, neurodegeneration-inhibiting activity, β-amyloid toxicity-inhibiting activity, neuroneogenesis- and neuroregeneration-promoting activity, and proliferation- or differentiation-promoting activity in nerve stem cell and/or neuron, and are useful as a drug for a mammal including a human. In addition, Compound (I) is useful not only as an intermediate for synthesizing Compounds (XI) and (XII) but also as a lipid peroxide production-inhibiting agent.

More specifically, Compound (I), Compound (XI) and Compound (XII) are effective for nerve degenerative diseases (e.g., Alzheimer's disease, Parkinson's disease amyotrophic lateral sclerosis (ALS), Huntington's disease, spinocerebellar degeneration etc.), psychoneurotic diseases (e.g., schizophrenia etc.), head injury, spinal cord injury, cerebrovascular accident, cerebrovascular dementia, peripheral neuropathy (e.g., diabetic neuropathy etc.) and the like, and are used as an agent for preventing or treating these diseases. In addition, Compound (I) is useful as an agent for preventing or treating circulatory diseases such as cerebral stroke, inflammatory and the like.

Compounds (I), (XI) and (XII) can be formulated into a pharmaceutical composition or preparation according to the methods described, for example, in EP483772A and WO 00/34262, and can be used as an agent for preventing or treating the above-mentioned diseases.

The following Examples and Reference Examples explain the present invention more particularly, but do not intend to limit the present invention.

EXAMPLE 1

Preparation of 2-methyl-1-(4-methylphenyl)-2-(2,3,5-trimethylphenoxy)-1-propanone A solution of 2-bromo-2-methyl-1-(methylphenyl)-1-propanone (422 g) in dimethyl sulfoxide (DMSO, 681 mL) was added dropwise to a solution of 2,3,5-trimethylphenol (136.19 g) and potassium carbonate (276.4 g) in DMSO (681 mL), followed by stirring at 35° C. for 24 hours. To the mixture were added dropwise methanol (953 mL) warmed to 55° C. and then water (953 mL). The mixture was stirred at 55° C. for 30 minutes and then at 40° C. for 1 hour. Precipitated crystals were filtered and suspended in methanol (2043 mL). Water (681 mL) was added to the suspension and the mixture was stirred at 40° C. for 1 hour. Precipitated crystals were filtered to obtain the title compound (257.98 g, 87%).

$^1$H-NMR(CDCl$_3$) δ: 1.65(6H,s), 2.05(3H,s), 2.17(3H,s), 2.20(3H,s), 2.36(3H,s), 6.18(1H,s), 6.55(1H,s), 7.18(2H,d, J=8.3 Hz), 8.23(2H,d,J=8.3 Hz).

EXAMPLE 2

Preparation of 2-methyl-1-(4-methylphenyl)-2-(2,3,5-trimethylphenoxy)-1-propanol A solution of sodium borohydride (25.7 g) in 0.1N NaOH (202 mL) was added dropwise to a suspension of 2-methyl-1-(4-methylphenyl)-2-(2,3,5-trimethylphenoxy)-1-propanone (251.9 g) in methanol (2519 mL). The mixture was stirred at 35° C. for 3 hours. After the mixture was adjusted to pH 7 by addition of 1N HCl under ice-cooling, methanol was distilled off, followed by extraction with toluene (2015 mL). The extract was washed, and the solvent was distilled off to quantitatively obtain the title compound as an oil (253.7 g).

$^1$H-NMR(CDCl$_3$) δ: 1.11(3H,s), 1.22(3H,s), 2.14(3H,s), 2.23(3H,s), 2.26(3H,s), 2.34(3H,s), 3.38(1H,bs), 4.87(1H,s), 6.72(1H,s), 6.75(1H,s), 7.14(2H,d,J=8.3Hz), 7.34(2H,d, J=8.3 Hz)

EXAMPLE 3

Preparation of 2,2,4,6,7-pentamethyl-3-(4-methylphenyl)-2,3-dihydro-1-benzofuran Trifluoromethanesulfonic acid (7.5 mL) was added to a solution of 2-methyl-1-(4-methylphenyl)-2-(2,3,5-trimethylphenoxy)-1-propanol (253.7 g) obtained in Example 2 in toluene (1260 mL), and the mixture was stirred at 50° C. for 30 minutes and then for 1 hour under reflux. To the mixture was added 1N NaOH (756 mL) at 25° C. The toluene layer was separated and washed with water, and the solvent was distilled off. The residue was dissolved in isopropanol (1511 mL) and water (756 mL) was added thereto. Precipitated crystals were filtered to obtain the title compound (176.33 g, 74%).

$^1$H-NMR(CDCl$_3$) δ: 1.01(3H,s), 1.49(3H,s), 1.83(3H,s), 2.14(3H,s), 2.23(3H,s), 2.30(3H,s), 4.09(1H,s), 6.72(1H,s), 6.48(1H,s), 6.48-7.05(4H, br).

EXAMPLE 4

Preparation of 5-bromo-2,2,4,6,7-pentamethyl-3-(4-methylphenyl)-2,3-dihydro-1-benzofuran Bromine (29.3 mL) was added dropwise to a mixture of 2,2,4,6,7-pentamethyl-3-(4-methylphenyl)-2,3-dihydro-1-benzofuran (145 g), sodium acetate (50.9 g) and acetonitrile (2175 mL) at 0 to 5° C. The mixture was stirred at 0 to 10° C. for 1 hour and water (725 mL) was added thereto. Precipitated crystals were filtered to obtain the title the compound (175 g, 94.2%).

$^1$H-NMR(CDCl$_3$) δ: 1.01(3H,s), 1.48(3H,s), 1.97(3H,s), 2.22(3H,s), 2.30(3H,s), 2.39(3H,s), 4.13(1H,s), 6.50-7.05 (4H,br)

EXAMPLE 5

Preparation of N-benzyl-2,2,4,6,7-pentamethyl-3-(4-methylphenyl)-2,3-dihydro-1-benzofuran-5-amine Under a nitrogen atmosphere, to toluene (500 mL) were added 5-bromo-2,2,4,6,7-pentamethyl-3-(4-methylphenyl)-2,3-dihydro-1-benzofuran (100 g) and benzylamine (36.5 mL), then palladium acetate (62.5 mg) and 2,2'-bis(diphenylphosphinino)-1,1'-binaphthyl [(BINAP, 0.52 g)], and further t-BuONa (37.45 g). The mixture was stirred at 25° C. for 20 minutes and then at 107° C. for 24 hours. To the mixture were added dropwise 1N HCl (167 mL) and water (113 mL) at 70° C. or below, and the mixture was stirred for 10 minutes. The organic layer was separated and washed with a 10% aqueous sodium chloride solution, and the solvent was distilled off. The residue was crystallized from isopropanol-water to obtain the title compound (99 g, 92.3%).

$^1$H-NMR(CDCl$_3$) δ: 1.03(3H,s), 1.49(3H,s), 1.80(3H,s), 2.18(3H,s), 2.26(3H,s), 2.30(3H,s), 3.91(2H,s), 6.50-7.05 (4H,m), 7.22-7.37(5H,m).

EXAMPLE 6

Preparation of 2,2,4,6,7-pentamethyl-3-(4-methylphenyl)-2,3-dihydro-1-benzofuran-5-amine To a mixture of N-benzyl-2,2,4,6,7-pentamethyl-3-(4-methylphenyl)-2,3-dihydro-1-benzofuran-5-amine (80 g), toluene (240 mL) and isopropanol (80 mL) was added 10% Pd-carbon (a product containing 50% water, 4 g), and the mixture was hydrogenated at 35° C. under atmospheric pressure. After completion of the reaction, the catalyst was filtered. Concentrated hydrochloric acid (19.2 mL) was added to the filtrate and the mixture was stirred at 10° C. or below for 1 hour. Precipitated crystals were filtered. The crystals were added to a mixture of methanol (560 mL) and water (80 mL) and the mixture was heated to 50° C. to dissolve the crystals. Then, 25% aqueous ammonia water was added dropwise to the solution to adjust to pH 8.5. Precipitated crystals were filtered to obtain the title compound (54.32 g, 88.6%).

$^1$H-NMR(CDCl$_3$) δ: 0.99(3H,s), 1.47(3H,s), 1.77(3H,s), 2.12(2H,s), 2.19(3H,s), 2.30(3H,s), 3.20(2H,s), 3.20(2H,bs), 4.08(1H,s), 6.75(2H,b), 6.83-7.04(2H,m)

EXAMPLE 7

Preparation of 2,2,4,6,7-pentamethyl-3-(4-methylphenyl)-2,3-dihydro-1-bnezofuran Trifluoromethanesulfonic acid (92.4 mg) was added to a solution of 2-methyl-2-(4-methylphenyl)propionaldehyde (1.2 g) and 2,3,5-trimethylphenol (0.84 g) in toluene (8 mL). The mixture was heated to reflux for 1 hour. After cooling, 1N NaOH (5 mL) was added thereto and stirred at room temperature for 30 minutes. The organic layer was separated and washed with water, and the solvent was then distilled off. The residue was dissolved in isopropanol (3 mL) and water (5 mL) was added thereto. Precipitated crystals were filtered to obtain the title compound (1.3 g, 75.2%).

EXAMPLE 8

According to the same manner as that of Example 7, the following compounds were prepared.

1) 2,2,4,6,7-Pentamethyl-3-(4-methoxyphenyl)-2,3-dihydro-1-benzofuran $^1$H-NMR(CDCl$_3$) δ: 1.02(3H,s), 1.48(3H,s), 1.84(3H,s), 2.13(2H,s), 2.23(3H,s), 3.77(3H,s), 4.07(1H,s), 6.48(1H,s), 6.40-7.10(4H,m)

2) 2,2,4,6,7-Pentamethyl-3-phenyl-2,3-dihydro-1-benzofuran $^1$H-NMR(CDCl$_3$) δ: 1.02(3H,s), 1.51(3H,s), 1.83(3H,s), 2.14(2H,s), 2.23(3H,s), 4.12(1H,s), 6.49(1H,s), 6.40-7.25 (5H,m).

3) 3-(4-Chlorophenyl)-2,2,4,6,7-pentamethyl-2,3-dihydro-1-benzofuran $^1$H-NMR(CDCl$_3$) δ: 1.02(3H,s), 1.50(3H,s), 1.84(3H,s), 2.14(2H,s), 2.24(3H,s), 4.09(1H,s), 6.49(1H,s), 6.40-7.30 (5H,m).

4) 3-(4-Methoxyphenyl)-2,2,5-trimethyl-2,3-dihydro-1-benzofuran $^1$H-NMR(CDCl$_3$) δ: 0.96(3H,s), 1.55(3H,s), 2.25(3H,s), 3.80(3H,s), 4.26(1H,s), 6.70-7.02(7H,m).

5) 3-(4-Methylphenyl)-2,2,5-trimethyl-2,3-dihydro-1-benzofuran $^1$H-NMR(CDCl$_3$) δ: 0.96(3H,s), 1.55(3H,s), 2.24(3H,s), 2.33(3H,s), 4.26(1H,s). 6.70-7.15(7H,m).

6) 3-Phenyl-2,2,5-trimethyl-2,3-dihydro-1-benzofuran $^1$H-NMR(CDCl$_3$) δ: 0.96(3H,s), 1.57(3H,s), 2.25(3H,s), 4.27(1H,s), 6.71-7.33(8H,m).

7) 3-(4-Chlorophenyl)-2,2,5-trimethyl-2,3-dihydro-1-benzofuran $^1$H-NMR(CDCl$_3$) δ: 0.97(3H,s), 1.55(3H,s), 2.25(3H,s), 4.26(1H,s), 6.66-7.33(7H,m).

8) 3-(4-Chlorophenyl)-2,2-dimethyl-2,3-dihydro-1-benzofuran $^1$H-NMR(CDCl$_3$) δ: 1.77(3H,s), 1.78(3H,s), 4.62(1H,s), 6.73-7.26(8H,m).

9) 2,2-Dimethyl-3-(4-methylphenyl)-2,3-dihydro-1-benzofuran $^1$H-NMR(CDCl$_3$) δ: 1.78(3H,s), 1.79(3H,s), 2.32(3H,s), 4.67(1H,s), 6.70-7.12(8H,m).

10) 3-(4-Methylphenyl)-2,2,7-trimethyl-2,3-dihydro-1-benzofuran $^1$H-NMR(CDCl$_3$) δ: 1.78(3H,s), 1.79(3H,s), 2.32(3H,s), 2.31(3H,s), 4.52(1H,s), 6.66-7.15(7H,m).

11) 2-(3-Phenyl-4,6,7-trimethyl-2,3-dihydro-1-benzofuran)-spiro-1'-cyclopropane $^1$H-NMR(CDCl$_3$) δ: 2.00-2.05(1H,m), 2.15(3H,s), 2.20 (3H,s), 2.24(3H,s), 2.35-2.45(1H,m), 2.76-2.84(2H,m), 3.93 (1H,d), 6.56(1H,s), 7.15-7.60(5H,m).

EXAMPLE 9

Preparation of N-(3,4-dimethoxybenzyl)-2,2,4,6,7-pentamethyl-3-(4-methylphenyl)-2,3-dihydro-1-benzofuran-5-amine Under a nitrogen atmosphere, to toluene (1 mL) were added 5-bromo-2,2,4,6,7-pentamethyl-3-(4-methylphenyl)-2,3-dihydro-1-benzofuran (100 mg) and 3,4-dimethoxybenzylamine (56 mg), then palladium acetate (0.3 mg) and (S)-(−)-2,2'-bis(diphenylphosphino)-1,1'-binaphthyl (2.7 mg), and further sodium tert-butoxide (37.5 mg). The mixture was stirred at 80° C. for 17 hours. Ethyl acetate was added to the reaction mixture, insoluble materials were filtered and the filtrate was concentrated under reduced pressure. The residue was subjected to silica gel column chromatography, which was eluted with ethyl acetate-n-hexane [1:4], to obtain the title compound (80 mg, 64.5%).

$^1$H-NMR(300 MHz, CDCl$_3$) δ; 1.03(3H,s), 1.48(3H,s), 1.80(3H,s), 2.20(3H,s), 2.25(3H,s), 2.30(3H,s), 3.83(3H,s), 3.86(5H,s), 4.08(1H,s), 6.77-7.05(7H,m)

EXAMPLE 10

Preparation of 5,6-dimethoxy-2-(2,2,4,6,7-pentamethyl-3-(4-methylphenyl)-2,3-dihydro-1-benzofuran-5-yl)isoindoline Under a nitrogen atmosphere, to toluene (2 mL) were added 5-bromo-2,2,4,6,7-pentamethyl-3-(4-methylphenyl)-2,3-dihydro-1-bnezofuran (100 mg) and 4,5-dimethoxy-isoindoline (60 mg), then palladium acetate (1.25 mg) and (S)-(−)-2,2'-bis(diphenylphosphino-1,1'-dinaphthyl (10.4 mg), and further sodium tert-butoxide (37.5 mg). The mixture was stirred at 80° C. for 15 hours. Ethyl acetate was added to the reaction mixture, insoluble materials were filtered and the filtrate was concentrated under reduced pressure. The residue was subjected to silica gel column chromatography, which was eluted with ethyl acetate-n-hexane [1:6], to obtain the title compound (60 mg, 47.2%).

$^1$H-NMR(CDCl$_3$) δ: 1.01(3H,s), 1.48(3H,s), 1.76(3H,s), 2.17(3H,s), 2.18(3H,s), 2.30(3H,s), 3.87(6H,s), 4.09(1H,s), 4.45(4H,s), 6.76-7.06(6H,m).

EXAMPLE 11

Preparation of N—((R)-(+)-1-phenylethyl)-2,2,4,6, 7-pentamethyl-3-(4-methylphenyl)-2,3-dihydro-1-benzofuran-5-amine Under a nitrogen atmosphere, to toluene (10 mL) were added 5-bromo-2,2,4,6,7-pentamethyl-3-(4-methylphenyl)-2,3-dihydro-1-benzofuran (2 g) and (R)-(+)-1-phenylethylamine (0.94 g), then palladium acetate (5 mg) and (S)-(−)-2,2'-bis(diphenylphosphino)-1,1'-dinaphthyl (41.6 mg), and further sodium tert-botoxide (0.86 g). The mixture was stirred at 107° C. for 7 hours. Diluted hydrochloric acid was added to the reaction solution. The organic layer was washed with a 10% aqueous solution of sodium chloride and concentrated under reduced pressure. The residue was subjected to silica gel column chromatography, which was eluted with ethyl acetate-n-hexane [1:19], to obtain the title compound (2.12 g, 95.5%).

$^1$H-NMR(300 MHz,CDCl$_3$) δ: 0.98-1.02(3H,m), 1.41-1.69(9H,m), 2.08-2.31(9H,m) 3.96-4.16(2H,m), 6.5-7.02 (4H,m), 7.14-7.29(5H,m)

EXAMPLE 12

Preparation of N—((S)-(−)-1-phenylethyl)-2,2,4,6,7-pentamethyl-3-(4-methylphenyl)-2,3-dihydro-1-benzofuran-5-amine Under a nitrogen atmosphere, to toluene (10 mL) were added 5-bromo-2,2,4,6,7-pentamethyl-3-(4-methylphenyl)-2,3-dihydro-1-benzofuran (2 g) and (S)-(−)-1-phenylethylamine (0.94 g), then palladium acetate (5 mg) and (S)-(−)-2,2'-bis(diphenylphosphino)-1,1'-dinaphthyl (41.6 mg), and further sodium tert-butoxide (0.86 g). The mixture was stirred at 100° C. for 6 hours. Diluted hydrochloric acid was added to the reaction solution. The organic layer was washed with a 10% aqueous solution of sodium chloride and concentrated under reduced pressure. The residue was subjected silica gel column chromatography, which was eluted with ethyl acetate-n-hexane [1:19], to obtain the title compound (2.13 g, 96.0%).

$^1$H-NMR(300 MHz,CDCl$_3$) δ: 0.98-1.02(3H,m), 1.41-1.69(9H,m), 2.08-2.31(9H,m) 3.96-4.16(2H,m), 6.5-7.02 (4H,m), 7.14-7.29(5H,m)

REFERENCE EXAMPLE 1

Preparation of (+)-2,2,4,6,7-pentamethyl-3-(4-methylphenyl)-2,3-dihydro-1-benzofuran-5-amine A suspension of (+)-di-p-toluoyltartaric acid (1936 g) in isopropyl alcohol (14.8 L) was heated to 75° C. to dissolve and then a solution of 2,2,4,6,7-pentamethyl-3-(4-methylphenyl)-2,3-dihydro-1-benezofuran-5-amine (1850 g) in toluene (9250 mL) was added dropwise thereto. The mixture was stirred at the same temperature for 10 minutes and then at 67 to 69° C. for 30 minutes, and was cooled to room temperature (25 to 30° C.). Precipitated crystals were filtered and washed with toluene-isopropyl alcohol (5:1) to obtain a diastereomer salt (2234 g).

mp. 193-194° C., [α]$_D$=+79.2° (C=1.0, MeOH)

$^1$H-NMR(DMSO-d$_6$) δ: 0.88(3H,s), 1.37(3H, s), 2.01(3H, s), 2.05(3H,s), 2.24(3H,s), 2.39(6H,s), 4.08(1H,s), 5.80(2H, s), 7.03-7.26(6H, m), 7.27(4H, d, J=8.0), 7.89(4H, d,J=8.0).

A solution of a diasteromer salt in methanol (12.025 L) was heated to 45° C. and 25% aqueous ammonia was added dropwise to adjust to pH 8.5. The solution was stirred at 50° C. for 10 minutes and water (3105 mL) was added. After crystallization was observed, water (4163 mL) was further added and the mixture was stirred at 50° C. for 1 hour and then at 25 to 30° C. for 1 hour. The crystals were filtered and washed with 50% methanol to obtain the title compound (805.1 g, 43.5%).

mp. 91-92° C., [α]$_D$=+5.2° (C=1.0, MeOH).

$^1$H-NMR(CDCl$_3$) δ: 1.01(3H,s), 1.48(3H, s), 1.79(3H,s), 2.14(3H,s), 2.20(3H,s), 2.31(3H,), 3.08(2H,bs), 4.10(1H, s), 6.60-7.10(4H, m)

REFERENCE EXAMPLE 2

Preparation of (R)-(+)-5,6-dimethoxy-2-(2,2,4,6,7-pentamethyl-3-(4-methylphenyl)-2,3-dihydro-1-benzofuran-5-yl)isoindoline A solution of (+)-2,2,4,6,7-pentamethyl-3-(4-methylphenyl)-2,3-dihydro-1-benzofuran-5-amine (800 g) and N-ethyldiisopropylamine (943.2 mL) in toluene (3867 mL) was added dropwise to a solution of 1,2-bischloromethylveratrole (675.9 g) in toluene (4000 mL) under heating (inner temperature 100° C.) under a nitrogen atmosphere over 4.5 hours. After completion of addition, the mixture was further stirred at 100° C. for 1 hour. 0.5N HCl (1600 mL) was added thereto and the mixture was shaken. The organic layer was separated and washed with water. To the washed organic layer,methanol (1040 mL) was added at an inner temperature of 45° C. and concentrated hydrochloric acid (333.6 mL) was then added dropwise. Crystallization was observed. The reaction mixture was stirred at 50° C. for 30 minutes and then at 5° C. for 1 hour. The crystals were filtered and washed with toluene and then 50% ethanol to obtain (R)-(+)-5,6-dimethoxy-2-(2,2,4,6,7-pentamethyl-3-(4-methylphenyl)-2,3-dihydro-1-benzofuran-5-yl)isoindoline hydrochloride (1119 g, 83.6%). The crystals were dissolved in a mixture of 90% ethanol (5600 mL) and concentrated hydrochloric acid (110 mL), and 2,6-di-tert-butyl-4-hydroxytoluene (8.0 g) was added thereto. After 6.25% aqueous ammonia was added dropwise at 50° C. to adjust to pH 8.0, water (640 mL) was added. The mixture was stirred at 50° C. for 30 minutes and then at room temperature for 1 hour. Precipitated crystals were filtered and washed with 70% ethanol to obtain the title compound (935 g, 75.5%).

mp. 157-159° C., [α]$_D$=+62.3° (C=0.488, MeOH)

$^1$H-NMR(CDCl$_3$) δ: 1.01(3H,s), 1.48(3H,s), 1.76(3H,s), 2.17(3H,s), 2.18(3H,s), 2.30(3H,s), 3.87(6H,s), 4.09(1H,s), 4.45(4H,s), 6.76-7.06(6H,m).

INDUSTRIAL APPLICABILITY

As described above, according to the present invention, it is possible to introduce a substituent onto a 2,3-dihydrobenzofuran ring with good position-selectivity by using fewer steps and under milder reaction conditions than conventional methods. Therefore, the present invention provide a novel process suitable for industrially producing benzofuran derivatives useful as drugs, which suppresses side reaction and can attain a higher yield as a whole.

The invention claimed is:
1. A process for producing a compound represented by the formula:

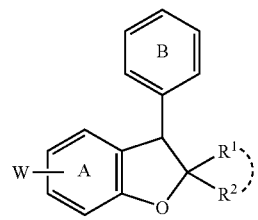

wherein ring A is a benzene ring that may be optionally further substituted in addition to the group represented by W, and other symbols are as defined below, or a salt thereof; which comprises reacting a compound represented by the formula:

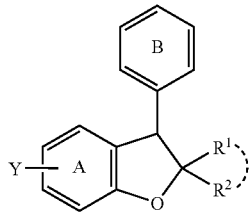

wherein R¹ and R² are the same or different and each is a hydrogen atom, an optionally substituted hydrocarbon group or an optionally substituted heterocyclic group, or R¹ and R² may be taken together with the adjacent carbon atom to form an optionally substituted 3- to 8-membered homocyclic or heterocyclic ring, Y is a halogen atom, ring A is a benzene ring that may be optionally further substituted in addition to the group represented by Y, and ring B is an optionally substituted benzene ring, or a salt thereof, with a compound represented by the formula:

WH wherein W is:
(i) a group represented by the formula:

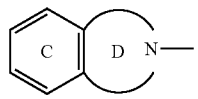

wherein ring C is an optionally substituted benzene ring, and ring D is a 5- to 7-membered nitrogen-containing heterocyclic ring that may be optionally substituted with halogen or an optionally substituted hydrocarbon group, or
(ii) a group represented by the formula:

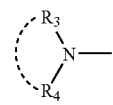

wherein R³ is (1) a hydrogen atom, (2) an aliphatic hydrocarbon group that is substituted with an optionally substituted aromatic group and may be optionally further substituted, or (3) an acyl group containing an optionally substituted aromatic group; R⁴ is a hydrogen atom, an optionally substituted hydrocarbon group or an acyl group; or R³ and R⁴ may be taken together with the adjacent nitrogen atom to form an optionally substituted 4- to 8-membered nitrogen-containing ring, or a salt thereof and thereafter, if necessary, deprotecting the resultant product.

2. The process according to claim 1, wherein W is at the 5-position on a 2,3-dihydrobenzofuran ring.

3. The process according to claim 1, which is for producing a compound represented by the formula:

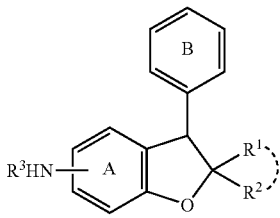

wherein R¹ and R² are the same or different and each is a hydrogen atom, an optionally substituted hydrocarbon group or an optionally substituted heterocyclic group, or R¹ and R² may be taken together with the adjacent carbon atom to form an optionally substituted 3- to 8-membered homocyclic or heterocyclic ring, ring A is a benzene ring that may be optionally substituted in addition to the group represented by R³HN, ring B is an optionally substituted benzene ring, and R³ is (1) a hydrogen atom, (2) an aliphatic hydrocarbon group that is substituted with an optionally substituted aromatic group and may be optionally further substituted or (3) an acyl group containing an optionally substituted aromatic group, or a salt thereof.

4. The process according to claim 1, wherein a compound represented by the formula:

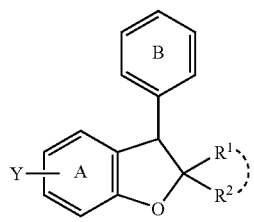

wherein R¹ and R² are the same or different and each is a hydrogen atom, an optionally substituted hydrocarbon group or an optionally substituted heterocyclic group, or R¹ and R² may be taken together with the adjacent carbon atom to form an optionally substituted 3- to 8-membered homocyclic or heterocyclic ring, Y is a halogen atom, ring A is a benzene ring that may be optionally further substituted in addition to the group represented by Y, and ring B is an optionally substituted benzene ring, or a salt thereof is produced by reacting a compound represented by the formula:

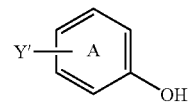

wherein Y' is a hydrogen atom or a halogen atom, ring A is a benzene ring that may be optionally further substituted in addition to the group represented by Y', and other symbols are as defined above, or a salt thereof with a compound represented by the formula:

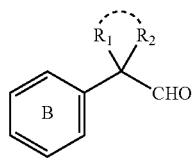

wherein each symbol is as defined above, or a salt thereof in the presence of an acid and thereafter, when Y' is a hydrogen atom, halogenating the reaction the product.

5. 5-Bromo-2,2,4,6,7-pentamethyl-3-(4-methylphenyl)-2,3-dihydro-1-benzofuran.

6. N-benzyl-2,2,4,6,7-pentamethyl-3-(4-methylphenyl)-2,3-dihydro-1-benzofuran-5-amine.

* * * * *